(12) United States Patent
Kang et al.

(10) Patent No.: US 11,144,124 B2
(45) Date of Patent: Oct. 12, 2021

(54) ELECTRONIC DEVICE AND CONTROL METHOD THEREOF

(71) Applicant: Samsung Electronics Co., Ltd., Suwon-si (KR)

(72) Inventors: Hyuk Kang, Yongin-si (KR); Jae-bong Yoo, Seongnam-si (KR); Kyung-soo Lim, Yongin-si (KR); Duk-ki Hong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/461,178

(22) PCT Filed: Nov. 16, 2017

(86) PCT No.: PCT/KR2017/013046
§ 371 (c)(1),
(2) Date: May 15, 2019

(87) PCT Pub. No.: WO2018/093181
PCT Pub. Date: May 24, 2018

(65) Prior Publication Data
US 2019/0369726 A1 Dec. 5, 2019

Related U.S. Application Data

(60) Provisional application No. 62/422,680, filed on Nov. 16, 2016.

(30) Foreign Application Priority Data

Apr. 11, 2017 (KR) .................. 10-2017-0046886
Nov. 16, 2017 (KR) .................. 10-2017-0153101

(51) Int. Cl.
*G06F 3/01* (2006.01)
*A61B 5/0205* (2006.01)
(Continued)

(52) U.S. Cl.
CPC ............ *G06F 3/015* (2013.01); *A61B 5/0205* (2013.01); *A61B 5/053* (2013.01); *A61B 5/0533* (2013.01);
(Continued)

(58) Field of Classification Search
None
See application file for complete search history.

(56) References Cited

U.S. PATENT DOCUMENTS 7,599,735 B2 10/2009 Viertio-Oja et al.
8,434,868 B2 5/2013 Sato et al.
(Continued)

FOREIGN PATENT DOCUMENTS

EP 1 637 975 A1 3/2006
JP H09-271466 A 10/1997
(Continued)

OTHER PUBLICATIONS

Extended European Search Report dated Oct. 18, 2019, issued in European Patent Application No. 17871993.6.
(Continued)

*Primary Examiner* — Matthew Yeung
(74) *Attorney, Agent, or Firm* — Jefferson IP Law, LLP

(57) ABSTRACT

An electronic device is disclosed. The electronic device comprises: a biological signal input unit for receiving the input of a biological signal detected through an electrode; and a processor which determines, based on a usage context of the electronic device, a biological signal to be inputted, sets up, according to the determined biological signal, the state of a channel corresponding to the electrode, and determines a biological change by using the biological signal inputted according to the set channel state.

15 Claims, 16 Drawing Sheets

(51) Int. Cl.
    *A61B 5/053*     (2021.01)
    *A61B 5/0533*     (2021.01)
    *A61B 5/00*     (2006.01)
    *A61B 5/25*     (2021.01)
    *A61B 5/296*     (2021.01)
    *A61B 5/304*     (2021.01)
    *A61B 5/398*     (2021.01)

(52) U.S. Cl.
    CPC ................ *A61B 5/25* (2021.01); *A61B 5/296* (2021.01); *A61B 5/304* (2021.01); *A61B 5/398* (2021.01); *A61B 5/6803* (2013.01); *A61B 2503/12* (2013.01)

(56) References Cited

U.S. PATENT DOCUMENTS

| | | | |
|---|---|---|---|
| 2004/0034645 A1* | 2/2004 | Manabe | A61B 5/0478 |
| 2006/0061544 A1 | 3/2006 | Min et al. | |
| 2009/0326406 A1* | 12/2009 | Tan | G06F 3/017 |
| | | | 600/546 |
| 2010/0022903 A1* | 1/2010 | Sitzman | A61B 5/0402 |
| | | | 600/509 |
| 2013/0096466 A1 | 4/2013 | Sarrafzadeh et al. | |
| 2013/0225128 A1* | 8/2013 | Gomar | G10L 17/22 |
| | | | 455/411 |
| 2014/0210745 A1* | 7/2014 | Chizeck | G06F 3/048 |
| | | | 345/173 |
| 2014/0293145 A1* | 10/2014 | Jones | G06F 3/044 |
| | | | 349/12 |
| 2016/0077636 A1* | 3/2016 | Jordan | G01B 7/003 |
| | | | 345/174 |
| 2016/0133257 A1 | 5/2016 | Namgoong et al. | |
| 2016/0162011 A1* | 6/2016 | Verma | G06F 1/3215 |
| | | | 345/173 |
| 2016/0256068 A1 | 9/2016 | Harrison | |
| 2016/0259986 A1 | 9/2016 | Yun et al. | |
| 2016/0284363 A1 | 9/2016 | Von Borstel et al. | |
| 2016/0342782 A1* | 11/2016 | Mullins | G06F 21/32 |
| 2017/0049352 A1* | 2/2017 | Mirov | A61B 5/6824 |

FOREIGN PATENT DOCUMENTS

| | | |
|---|---|---|
| JP | 2008-517636 A | 5/2008 |
| JP | 2011-125692 A | 6/2011 |
| KR | 10-2005-0031538 A | 4/2005 |
| KR | 10-2011-0111064 A | 10/2011 |
| KR | 10-1633057 B1 | 6/2016 |
| WO | 2006/026548 A | 3/2006 |

OTHER PUBLICATIONS

European Office Action dated Apr. 22, 2020, issued in European Patent Application No. 17871993.6-1216.
Indian Examination Report dated Jun. 1, 2021, issued in Indian Patent Application No. 201917023254.
Chinese Office Action dated Jun. 30, 2021, issued in Chinese Patent Application No. 201780082139.7.

* cited by examiner (a)

(b)

(a)

Eye Tracking

Lip Motion

Hands-free Controller (b)

(a)

Facial Expression   Avatars (b)

(a)

(b)

ELECTRONIC DEVICE AND CONTROL METHOD THEREOF

TECHNICAL FIELD

The disclosure relates to an electronic device and a control method thereof, and more particularly, to a wearable electronic device capable of sensing a biological signal of a user and a control method thereof.

BACKGROUND ART

Recently, as researches on wearable devices have progressed actively, various wearable devices are being released. Wearable devices that are currently available or anticipated to launch are smart watch, head mounted display (HMD) devices, smart belt, etc.

A HMD device is a wearable display device that may be worn as wearing glasses and may display an image. The HMD device is also called a face mounted display (FMD) because a display is disposed close to wearer's eyes. The HMD device may be combined with augmented reality technology, N-screen technology and the like beyond the simple display function to provide various conveniences to a user.

In particular, the HMD device may provide a surrounding image to provide a more real and realistic virtual space to the user. The surrounding image may represent visual information spread in all directions around the HMD device. Therefore, the HMD device may direct a direction in which a face of the user wearing the HMD device faces, and display an image corresponding to the direction in the surrounding image. Thereby, the user may feel that the user actually exists in the virtual space.

On the other hand, because the HMD device is an environment in which it is difficult to use a separate input device such as a keyboard or a mouse, a technology for sensing a biological signal of the user, receiving the sensed biological signal and controlling the HMD device is emerging. In order to sense the biological signal, a plurality of dry electrodes may be attached and used on a wear surface of the HMD device. In the related art, because all the biological signals of the user are input through a plurality of electrodes, there was inefficiency in an amount of computation and an amount of consumed power for processing the signals.

Therefore, in order to solve such inefficiency, there is a need for a solution for inputting and using only a biological signal necessary for each use situation of the HMD device.

DISCLOSURE

Technical Problem

The disclosure provides an electronic device capable of selectively receiving a desired biological signal of a user in consideration of a context and a control method thereof.

Technical Solution

According to an aspect of the disclosure, an electronic device includes a biological signal inputter configured to receive a biological signal sensed through an electrode; and a processor configured to determine a biological signal to be input based on a context of the electronic device, set a state of a channel corresponding to the electrode according to the determined biological signal, and determine a biological change using the biological signal input according to the set state of the channel.

The processor may activate a channel corresponding to an electrode for sensing the determined biological signal and deactivate a channel other than the channel corresponding to the electrode for sensing the determined biological signal.

The processor may determine the biological change through a channel corresponding to at least one electrode corresponding to a specific body part according to the context of the electronic device.

The electrode may include a first electrode used for sensing a first biological signal, and a second electrode used for sensing a second biological signal, and when the determined biological signal is the first biological signal, the processor may select a channel corresponding to the first electrode as a channel to receive the biological signal, and based on a characteristic of the first biological signal, set a state of the channel corresponding to the first electrode, and when the determined biological signal is the second biological signal, the processor may select a channel corresponding to the second electrode as the channel to receive the biological signal and based on a characteristic of the second biological signal, set a state of the channel corresponding to the second electrode.

The first electrode may be used to sense a safety signal at a left side, a right side and an upper side of user's eyes, and the second electrode may be used to sense an EMG signal at a lower side of the user's eyes.

The electrode may include a common electrode used for sensing any one of a plurality of biological signals determined based on the context of the electronic device, and the processor may select a channel corresponding to the common electrode as a channel to receive the determined biological signal, and set a state of the channel corresponding to the common electrode based on a characteristic of the determined biological signal.

The common electrode may be used for sensing any one biological signal of a safety signal and an EMG signal at a lower side of user's eyes.

The biological signal may include at least one of an electromyogram (EMG) signal, an electrooculogram (EOG) signal, an electroencephalogram (EEG) signal, an electrocardiogram (ECG) signal, a Galvanic skin response (GSR) signal, and a bioelectric impedance analysis (BIA) signal.

The processor may set at least one of a sampling rate, an analog-digital converter (ADC) resolution, and a cutoff frequency of a channel corresponding to an electrode for sensing the determined biological signal based on a characteristic of the determined biological signal.

Also, the processor may measure quality of the biological signal input, and determine a channel to which the determined biological signal is input based on the measured quality of the biological signal.

The electronic device may further include an outputter, wherein the processor may control the outputter to output a result according to the determined biological change.

The outputter may include a display, and the processor may control a screen of the display according to the determined biological change.

The context of the electronic device may include a display state of the display, and when the screen of the display is a screen for requesting user authentication using a mouth shape at the time of an utterance, the processor may determine an EMG signal around a user's mouth as a biological signal to be input, and may determine the biological change through a channel corresponding to an electrode for sensing the EMG signal.

Also, when the screen of the display is a screen operated by navigating, the processor may determine a safety signal as the biological signal to be input, and determine the biological change through a channel corresponding to an electrode for sensing the safety signal.

Also, when the screen of the display is a screen for performing facial recognition, the processor may determine an EMG signal and a safety signal as the biological signal to be input, and determine the biological change through a channel corresponding to an electrode for sensing the EMG signal and the safety signal.

Also, the EMG signal may be sensed by using a potential difference of a pair of electrodes adjacent to each other.

Further, the electronic device may further include a motion detection sensor, and the processor may selectively receive one of a safety signal corresponding to a left eye and a safety signal corresponding to a right eye according to a rotation direction of a user's head by using the motion detection sensor.

Further, the processor may determine a wearing state of the electronic device based on the biological signal sensed through an electrode for sensing the wearing state of the electronic device by a user and control the outputter to output a result according to the determination.

Also, when a signal of a threshold value or less is detected from at least one electrode for sensing wearing of the electronic device by the user, the processor may determine that the electronic device is in a non-wearing state and deactivate an electrode other than the at least one electrode for sensing the wearing of the electronic device.

Also, when the context of the electronic device requires recognition of a user's emotion, the processor may determine the biological change of the user through a channel corresponding to an electrode for sensing at least one of an EEG signal indicating a degree of concentration occurring in the frontal region, a skin electrical conductivity signal indicating a change in hydration degree of the skin on a face, and a bioelectrical resistance analyzing signal on the face, and recognize the user's emotion using the determined biological change.

According to another aspect of the disclosure, a control method of an electronic device includes determining a biological signal to be input based on a context of the electronic device; setting a state of a channel corresponding to an electrode for sensing the determined biological signal according to the determined biological signal; and determining a biological change using the biological signal input according to the set state of the channel.

At this time, the setting may include activating a channel corresponding to an electrode for sensing the determined biological signal and deactivating a channel other than the channel corresponding to the electrode for sensing the determined biological signal.

Also, the determining may include determining the biological change through a channel corresponding to at least one electrode corresponding to a specific body part according to the context of the electronic device.

Also, the electrode may include a first electrode used for sensing a first biological signal, and a second electrode used for sensing a second biological signal, and when the determined biological signal is the first biological signal, the setting may select a channel corresponding to the first electrode as a channel to receive the biological signal, and based on a characteristic of the first biological signal, set a state of the channel corresponding to the first electrode, and when the determined biological signal is the second biological signal, the setting may select a channel corresponding to the second electrode as the channel to receive the biological signal and based on a characteristic of the second biological signal, set a state of the channel corresponding to the second electrode.

Also, the first electrode may be used to sense a safety signal at a left side, a right side and an upper side of user's eyes, and the second electrode may be used to sense an EMG signal at a lower side of the user's eyes.

Also, the electrode may include a common electrode used for sensing any one of a plurality of biological signals determined based on the context of the electronic device, and the setting may select a channel corresponding to the common electrode as a channel to receive the determined biological signal, and set a state of the channel corresponding to the common electrode based on a characteristic of the determined biological signal.

Also, the common electrode may be used for sensing any one of a safety signal and an EMG signal at a lower side of user's eyes.

Also, the biological signal may include at least one of an electromyogram (EMG) signal, an electrocardiogram (EOG) signal, an electroencephalogram (EEG) signal, an electrocardiogram (ECG) signal, a Galvanic skin response (GSR) signal, and a bioelectric impedance analysis (BIA) signal.

Also, the setting may include setting at least one of a sampling rate, an analog-digital converter (ADC) resolution, and a cutoff frequency of a channel corresponding to an electrode for sensing the determined biological signal based on a characteristic of the determined biological signal.

Also, the control method may further include measuring quality of the biological signal sensed through the electrode, and determining a channel to which the biological signal is input based on the measured quality of the biological signal.

Also, the control method may further include outputting a result according to the determined biological change.

Also, the outputting may include controlling a screen of a display included in the electronic device according to the determined biological change.

Also, the context of the electronic device may include a display state of the display, and wherein when the screen of the display is a screen for requesting user authentication using a mouth shape at the time of an utterance, the determining includes determining an EMG signal around a user's mouth as a biological signal to be input.

Also, when the screen of the display is a screen operated by navigating, the determining may include determining a safety signal as the biological signal to be input.

Also, the context of the electronic device may include a screen state of the display, and when the screen of the display is a screen for performing facial recognition, the determining may include determining an EMG signal and a safety signal as the biological signal to be input.

Also, the EMG signal may be sensed by using a potential difference of a pair of electrodes adjacent to each other.

Further, the determining may include selectively determining one input of a safety signal corresponding to a left eye and a safety signal corresponding to a right eye according to a rotation direction of a user's head sensed by using a motion detection sensor.

Further, the control method may further include determining a wearing state of the electronic device based on the biological signal sensed through an electrode for sensing the wearing state of the electronic device by a user and outputting a result according to the determination.

Also, when a signal of a threshold value or less is detected from at least one electrode for sensing wearing of the electronic device by the user, the control method may further include deactivating an electrode other than at least one electrode for sensing the wearing of the electronic device.

Also, when the context of the electronic device requires recognition of a user's emotion, the determining may include determining at least one of an EEG signal indicating a degree of concentration occurring in the frontal region, a skin electrical conductivity signal indicating a change in hydration degree of the skin on a face, and a bioelectrical resistance analyzing signal on the face as the biological signal to be input.

Effect of Invention

According to various embodiments of the disclosure, in an HMD device controlled using a biological signal, only a necessary biological signal may be received and used according to a context of the HMD device, and thus an amount of computation and an amount of power consumption required for controlling the HMD device may be reduced and the convenience of a user may be increased.

BEST MODE

Figure 1A:
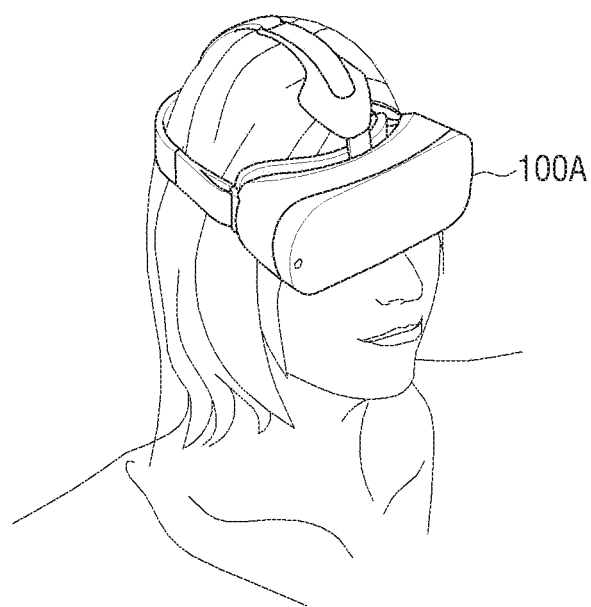
FIGS. 1(a) and 1(b) are diagrams for explaining an implementation example of an electronic device according to an embodiment of the disclosure.

Before describing the disclosure in detail, a method of describing the present specification and drawings will be described.

Firstly, general terms used in the present specification and claims are selected in consideration of functions of various embodiments of the disclosure. However, these general terms may vary according to intentions of one of ordinary skill in the art, legal or technical interpretation, the advent of new technologies, and the like. Also, some of the terms used herein may be arbitrarily chosen by the present applicant. In this case, these terms may be construed as meaning as defined herein and may be interpreted based on the overall content of the specification and common technical knowledge in the art unless there is a specific term definition.

Also, the same reference numerals or signs in the drawings attached to the present specification indicate components or elements that perform substantially the same function. For convenience of explanation and understanding, different embodiments will be described using the same reference numerals or signs. In other words, even though all the elements having the same reference numerals are shown in the plural drawings, the plural drawings do not mean an embodiment.

Also, in this specification and claims, terms including ordinal numbers such as 'first', 'second', etc. may be used for distinguishing between elements. Such an ordinal number is used to distinguish the same or similar elements from one another, and the use of such ordinal numbers should not be construed as limiting the meaning of the term. For example, elements in combination with such ordinal numbers should not be limited and construed in their use order or placement order. If necessary, each ordinal number may be used interchangeably.

As used herein, the singular forms "a", "an" and "the" include plural forms unless the context clearly dictates otherwise. In the present application, the terms "include" or "configure" and the like, specify the presence of a feature, a number, a step, an operation, an element, a component, or a combination thereof but do not preclude the presence or addition of one or more features, numbers, steps, operations, components, parts, or combinations thereof.

In an embodiment of the disclosure, the terms "module", "unit" and or "part" are terms to refer to an element performing at least one function or operation and may be implemented as hardware, software, or a combination of hardware and software. Also, a plurality of "modules", a plurality of "units", and a plurality of "parts" may be implemented as at least one processor (not shown) integrated into at least one module or chip, except for a "module", a "unit", or a "part" that is necessarily implemented as specific hardware.

Further, in an embodiment of the disclosure, when a part is connected to another part, this includes not only a direct connection but also an indirect connection through another medium. Also, a part including an element means that it may further include other elements, not the exclusion of any other elements, unless specifically stated otherwise.

Hereinafter, the disclosure will be described in detail with reference to the accompanying drawings.

Figure 1B:
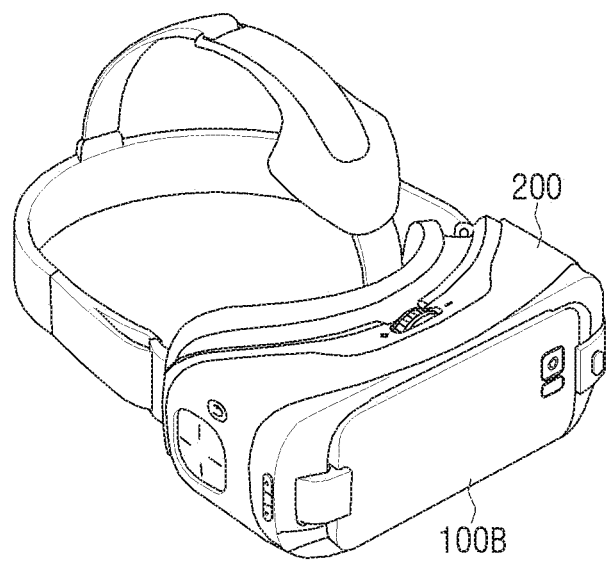

FIGS. 1(a) and 1(b) are diagrams for explaining an implementation example of an electronic device according to an embodiment of the disclosure.

The electronic device 100 of the disclosure may be implemented as an HMD (Head Mounted Display) device which may be worn on a user's head or worn around the eyes like glasses to provide VR contents. At this time, the electronic device 100 may be implemented as an integrated HMD device in which a band for worn on a user's head and various user interfaces and displays are integrally implemented, or a portable terminal device including a display such as a smart phone, etc. and may be detached and used in a removable HMD device (case) without a display.

FIG. 1(a) shows a user wearing the electronic device 100 implemented as the integrated HMD device 100A. Here, the electronic device 100 may be worn in the form of fixing a forehead and an occipital region of a user with a velcro type band to block the view of an external environment of the user in addition to contents provided by the electronic device 100.

FIG. 1(b) shows an appearance of the electronic device 100 implemented as the portable terminal device 100B attached to the removable HMD device 200. As shown in FIG. 1(b), the electronic device 100 may be implemented as a smart phone to provide a display to the user, and may be detached from and attached to a body of the removable HMD device 200 that is fixed to the forehead and the occipital region of the user.

The removable HMD device 200 may include an electrode capable of sensing a biological signal of the user, a button capable of receiving a user input, a communication module capable of performing wired/wireless communication with the electronic device 100. A specific configuration of the removable HMD device 200 will be described later.

In the embodiment shown in FIG. 1(b), the electronic device 100 is not limited to the smart phone. The electronic device 100 may be implemented as various devices including a display such as a tablet PC, a mobile phone, a video phone, an e-book reader, a PDA (Personal Digital Assistant), a PMP (portable multimedia player), an MP3 player, a navigation, a camera, and the like.

Figure 2A:
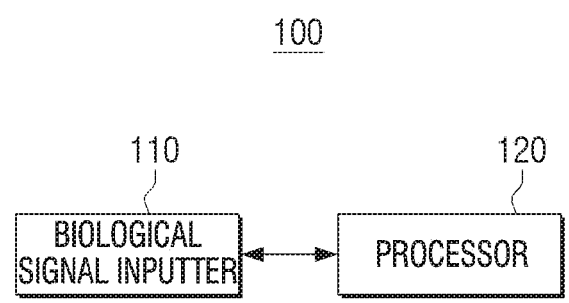
FIGS. 2(a) and 2(b) are block diagrams illustrating a brief configuration of an electronic device according to an implementation example of the disclosure.
Figure 2B:
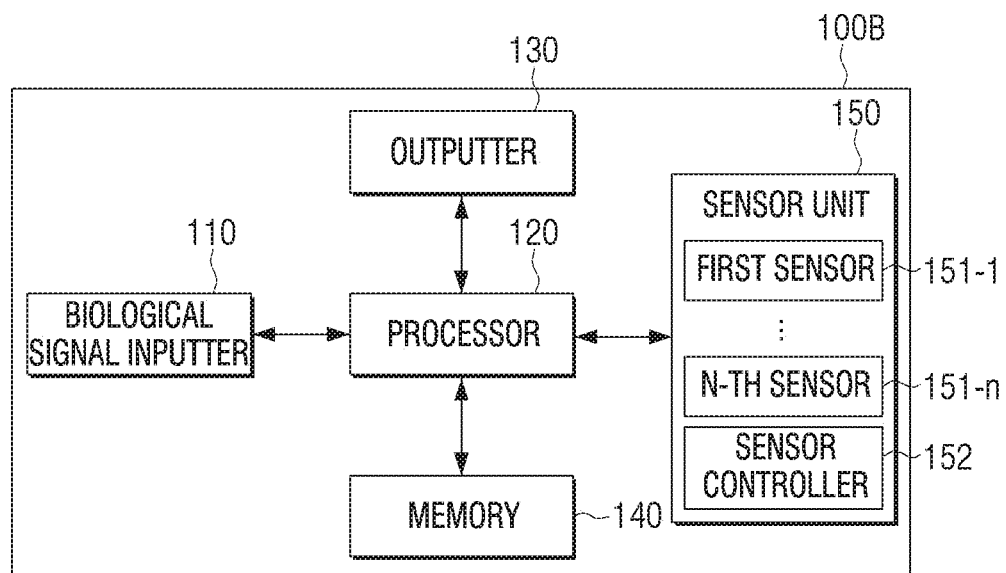

FIGS. 2(a) and 2(b) are block diagrams illustrating a brief configuration of the electronic device according to an implementation example of the disclosure.

According to FIG. 2(a), the electronic device 100 according to an embodiment of the disclosure indispensably includes a biological signal inputter 110 and a processor 120.

The biological signal inputter 110 is a configuration for receiving a biological signal of a user. Here, the user may refer to a wearer wearing the electronic device 100, and the biological signal may be obtained mainly from a user's face which is a part where the electronic device 100 is worn. Here, the biological signal mainly refers to a bioelectrical signal which is generated by electrochemical actions of excitable cells which are components of nerve, muscle, and glandular tissues. The electronic device 100 measures a desired biological signal using a sensor such as an electrode, and then performs signal processing.

However, the biological signal may be acquired through various parts of a user's body other than the user's face, and in a broad sense may include a signal sensed by a user's physical motion (hair rotation, nodding, etc.) other than the bioelectrical signal.

The biological signal as the bioelectrical signal may be a signal including at least one of an electromyogram (EMG) signal, an electrooculogram (EOG) signal, an electroencephalogram (EEG) signal, an electrocardiogram (ECG) signal, a Galvanic skin response (GSR) signal, and a bioelectric impedance analysis (BIA) signal.

The EMG signal is a signal that indicates the movement of a muscle, and is an electrical signal generated by the muscle movement of the user's face. The EMG signal is basically measured from an electrical signal generated by a physiological change occurring in a muscle fiber membrane. In the disclosure, the EMG signal is an electrical signal generated mainly through the muscle movement around the mouth, such as when the user speaks or bites molar. The biological signal inputter 110 may receive an electrical signal sensed from an electrode attached (particularly, below the eyes) to the periphery of the eye as the EMG signal.

The EOG signal is an electrical signal generated by the movement of the eye due to a voltage difference between the cornea of the user. A constant potential between the cornea (+) and the retina (−) of the eye exists to serve as a constant dipole. To measure this, the biological signal inputter 110 may receive an electrical signal sensed from electrodes attached to the left and right sides of the eye as the EOG signal. Specifically, when the user gazes at the front, the constant dipole is formed between two electrodes, and an output at this time becomes zero (0). When the user gazes at the left side, the + component is output. When the user gazes at the right side, the − component is output. Thus the + and − components are changed according to polarity of the electrodes and direction of the movement. The EOG signal may also be used to measure the flicker of the user's eyes. The electrodes are attached to the upper and lower sides of one eye and then measured.

The EEG signal is an electrical signal that is generated when a signal is transmitted between a nervous system and a cranial nerve. The EEG signal is different according to a state of mind and body, and is the most important indicator for measuring an activity status of the brain. The EEG signal is generally sensed through an electrode attached to the scalp, and the biological signal inputter 110 may receive an electrical signal sensed from an electrode attached to the forehead as the EEG signal.

The ECG signal is an electrical signal generated by the contraction and relaxation of the heart and is the most representative biological signal that may be measured easily and quickly on the body surface. A heart motion is expressed in beats per minute (bpm), and changes in the autonomic nervous system may be seen through changes in the heart rate. The ECG signal may also be measured on the user's face, and the biological signal inputter 110 may receive an electrical signal sensed from electrodes attached to various parts as the ECG signal.

The GSR signal is a signal that is generally used as an indicator of an emotional state, and is a biological signal for measuring the electrical resistance of the skin. For example, in a general arousal state, the electrical resistance of the skin is reduced, and the GSR signal may indicate a degree of an electrical resistance change of the skin according to such a characteristic. That is, the GSR signal is related to the activity of the sweat glands.

The BIA signal is a signal measured by using a method of flowing alternating current to the extent that it does not harm the human body and is a biological signal that may measure an amount of water in the body. The basic principle of the BIA is to estimate the body composition using an electrical resistance measured when a weak alternating current is flowed through the body using the characteristic that the current flows along a part with the highest conductivity. Body fat tissues which contain a great amount of water have low resistance and excellent conductivity, and body fat tissues which contain little water have low conductivity and a high resistance, which is reflected to the BIA signal.

However, the biological signal may include various kinds of biological signals in addition to the above-mentioned signals.

Also, the biological signal inputter 110 may further include an electrostatic discharge (ESD) prevention circuit (not shown) for preventing an electrostatic discharge phenomenon.

On the other hand, the biological signal may be sensed through an electrode. The biological signal inputter 110 may receive a biological signal sensed from at least one electrode by wired or wirelessly. According to an embodiment, the electrode for sensing the biological signal may be included in the electronic device 100 or may be configured separately from the electronic device 100.

Specifically, in an embodiment in which the electronic device 100 of the disclosure is implemented as the integrated HMD device 100A, at least one electrode may be included in the biological signal inputter 110. In an embodiment in which the electronic device 100 of the disclosure is implemented as the removable HMD device 200 and the detached portable terminal device 100B, at least one electrode is included in the removable HMD device 200, and the biological signal inputter 110 may receive a biological signal sensed from the electrode included in the removable HMD device 200 by wired or wirelessly.

On the other hand, an Ag/AgCl electrode generally used in the measurement of a biological signal has good signal transmission, but is not reused and may have various side effects. Therefore, the electrode of the disclosure may not use an electrolyte between the skin and the electrode, and may use a dry electrode made of a metal such as stainless steel or copper. The dry electrode converts a bio-potential signal generated by ions in the body into an electrical signal.

On the other hand, the electrode may include an electrode for sensing a specific single kind of biological signal, an electrode (hereinafter, referred to as a common electrode) for sensing a plurality of kinds of biological signals, a reference electrode, a ground electrode, etc. The reference electrode may be separated from the ground electrode to be in contact with the body. The reference electrode and the ground electrode may configure a circuit as the same electrode. In an embodiment of the disclosure, it is assumed that the reference electrode and the ground electrode are used as the same electrode for the sake of convenience. Each of the electrodes needs to sense a biological signal around a user's eye, which is a position where the electronic device 100 is fixedly mounted. Therefore, the electronic device 100 implemented as the integrated HMD device 100A or the removable HMD device 200 may be disposed at a contact position around the eye and may be disposed at different positions for each kind of biological signals to be sensed. An attachment position and a function of each electrode will be described later with reference to FIG. 3.

On the other hand, the processor 120 is a configuration for controlling the overall operation of the electronic device 100.

In particular, the processor 120 may determine a biological signal to be input based on a context of the electronic device 100. Here, the context of the electronic device 100 refers to a current internal/external use condition of the electronic device 100, and specifically may include a context such as, a current geographical position of the electronic device 100 or a relative position with respect to a specific object, a current time and a relative time based on a specific time point, weather, a current operation state of the user, or biometric information of the user determined through a biological signal, etc.

Also, the context may include a screen state of a display 131 included in the electronic device 100, and a usage history. The screen state of the display 131 may include information about a currently executed application or contents being displayed, and information about a change of a screen. The usage history may include information about applications executed or contents displayed from the past to the present.

The electronic device 100 may further include various sensors (an acceleration sensor, a gyro sensor, a geomagnetic sensor, a temperature sensor, etc.) for determining the context and a communication module for receiving information from an external server over a network including Internet, etc.

The processor 120 may determine a type of the biological signal to be input based on the determined context. For example, when user authentication is required to use a specific application in the electronic device 100, a screen requesting user authentication may be displayed on the display 131. User authentication may be required when unlocking the electronic device 100, logging in to a specific web site, watching a specific content, or using electronic payment or the like.

At this time, user authentication may be performed through a muscle movement (in particular, a muscle movement around the mouth) of the face corresponding to the utterance of a specific word or sentence, and in this case, sensing of an EMG signal is required. When the determined context is determined that as 'user authentication', the processor 120 may determine the EMG signal around the user's mouth as the biological signal to be input.

In particular, at this time, the processor 120 may determine a biological change through a channel corresponding to at least one electrode corresponding to a specific body part according to the context of the electronic device 100 among electrodes for sensing the determined EMG signal. For example, in the context for sensing a motion in a mouth shape according to the user utterance, the processor 120 may control to sense the EMG signal through an electrode attached around the user's mouth.

Also, after user authentication is performed in the electronic device 100, a navigating screen such as a home screen for selecting a specific application, a selection screen for selecting a specific content, a screen for moving a cursor or a screen, etc. may be displayed. At this time, navigating may be performed through a movement of the pupils moving up and down and left and right, and in this case, sensing of an EOG signal is required. When the determined context is determined as 'navigating', the processor 120 may determine the EOG signal as the biological signal to be input.

On the other hand, when the type of the biological signal to be input is determined, a channel corresponding to an electrode (hereinafter, referred to as a target electrode) for sensing the determined type of the biological signal may be selected, a state of the channel corresponding to the selected electrode may be set according to the determined type of the biological signal, and a biological change may be determined by using the biological signal input according to the set state of the channel.

Specifically, an embodiment that the electrode includes a first electrode used for sensing a first biological signal and a second electrode used for sensing a second biological signal may be assumed. At this time, when the determined biological signal is the first biological signal, the processor 120 may select a channel corresponding to the first electrode as a channel to receive the biological signal and set a state of the channel corresponding to the first electrode based on a characteristic of the first biological signal. When the determined biological signal is the second biological signal, the processor 120 may select a channel corresponding to the second electrode as the channel to receive the biological signal and set a state of the channel corresponding to the second electrode based on a characteristic of the second biological signal.

In this case, the first electrode may be an electrode used to sense the EOG signal on left, right, and upper sides of the user's eyes. Also, the second electrode may be an electrode used to sense the EMG signal on a lower side of the user's eyes.

For example, when a type of the biological signal to be input is determined to be the EOG signal, the processor 120 may set a sampling rate of the channel corresponding to a target electrode for sensing the EOG signal, an ADC (Analog Digital Converter) resolution, a cutoff frequency and the like according to characteristics of the EOG signal. Accordingly, other biological signals (the EMG signal, the ECG signal, etc.) sensed by the target electrode for sensing the EOG signal may be removed.

The processor 120 may determine a biological change (a movement of a pupil or a movement of a facial muscle) using a biological signal input from the target electrode according to the set state of the channel.

Also, the processor 120 may control the screen of the display 131 according to the determined biological change. For example, the processor 120 may select a menu or an icon or perform a navigating operation according to the movement of the pupil or a flicker of the eye when the determined biological change is the movement of the pupil or the flicker of the eye using the EOG signal. Also, when the determined biological change is the muscle movement using the EMG signal, the processor 120 may determine a mouth shape of the user according to the movement of the muscle, perform user authentication, or determine a face movement such as wink.

Also, when the biological signal to be input is determined, the processor 120 may activate only the channel corresponding to the electrode for sensing the determined biological signal, and deactivate a channel other than the channel corresponding to the electrode for sensing the determined biological signal, and thus power waste consumed by an unused electrode may be reduced.

Figure 2B:
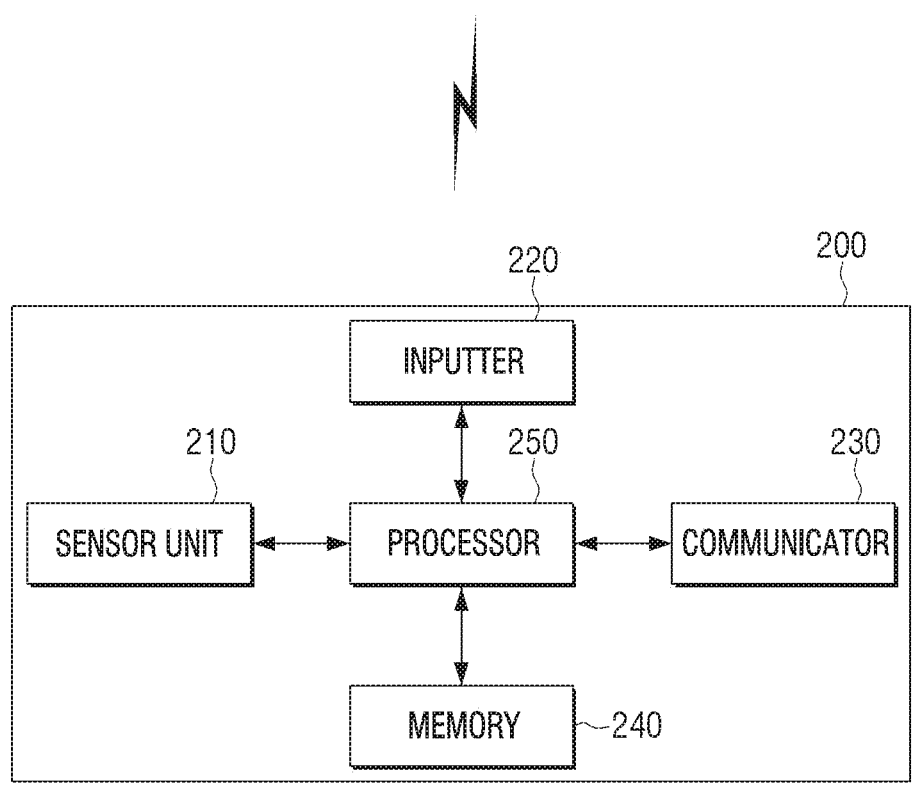

FIG. 2(*b*) is a detailed block diagram showing a configuration of the electronic device 100 according to another embodiment of the disclosure.

It is assumed that FIG. 2(*b*) is an example in which the electronic device 100 implemented as the portable terminal device 100B is attached to the removable HMD device 200 and embodied. The electronic device 100 further includes an outputter 130, a memory 140 and a sensor unit 150, in addition to the biological signal inputter 110 and the processor 120. The description already provided in FIG. 2(*a*) will be omitted.

The removable HMD device 200 includes a sensor unit 210 for sensing a biological signal of a user, an inputter 220 for receiving a user input, a communicator 230 for communicating with the electronic device 100, and a memory 240.

The biological signal inputter 110 of the electronic device 100 is a configuration to receive a sensed biological signal from the removable HMD device 200. As shown in FIG. 2(*b*), when the electronic device 100 is implemented as the portable terminal device 100B attached to the removable HMD device 200, the biological signal inputter 110 may include a communication module for performing communication with the removable HMD device 200 by wired and wirelessly. Communication with the removable HMD device 200 using the communication module may be performed in various ways. Communication between the electronic device 100 and the removable HMD device 200 may be performed in at least one of NFC, Wi-Fi, Wi-Fi Direct, Zigbee, and Bluetooth.

The outputter 130 is a configuration to output at least one of an image signal and a sound signal. The outputter 130 may include a display 131 for outputting the image signal and may further include an audio outputter 132 for outputting the sound signal.

The display 131 is a configuration for providing a screen including various contents reproducible by the electronic device 100. Here, the contents may include contents in various formats such as text, image, moving picture, GUI (Graphic User Interface) and the like. In particular, the content may be implemented as VR (Visual Reality) contents for providing a 3D image.

An implementation method of the display 131 is not limited. For example, the display 131 may be implemented as a display in various forms such as an LCD (Liquid Crystal Display), an OLED (Organic Light Emitting Diodes) display, an AM-OLED (Active-Matrix Organic Light-Emitting Diode), a PDP (Plasma Display Panel), and the like. The display 131 may additionally include an additional configuration according to its implementation. For example, when the display 131 is a liquid crystal type, the display 131 includes an LCD display panel (not shown), a backlight unit (not shown) for supplying light thereto, and a panel driving substrate (not shown) for driving the panel (not shown).

The audio outputter 132 may be implemented as a speaker that outputs audio data (sound signals) processed by the electronic device 100.

The processor 120 may control the display 131 or the audio outputter 132 to output a result according to the determined biological change. That is, the processor 120 may control sound output through the screen of the display 131 or the audio outputter 132 according to the determined biological change.

Also, the processor 120 may determine a wearing state of the removable HMD device 200 based on the biological signal sensed by the user through the electrode for sensing the wearing state of the removable HMD device 200, and control the outputter 130 to output a result according to determination. For example, when the wearing state of the electronic device 100 is defective, the processor 120 may output a warning message or a warning alarm to wear the removable HMD device 200 properly.

At this time, the processor 120 may determine that the removable HMD device 200 is in a non-wearing state when a signal of a threshold value or less is detected from at least one electrode for sensing the wearing state of the removable HMD device 200 by the user, and deactivate a channel corresponding to an electrode other than the at least one electrode for sensing the wearing of the removable HMD device 200.

The memory 140 may store O/S (Operating System) software module for driving the electronic device 100, and various data such as various multimedia contents including VR contents.

The sensor unit 150 includes first to n-th sensors 151-1 to 151-*n* for sensing various operations performed in the electronic device 100 and a sensor controller 152 for controlling the first to n-th sensors 151-1 to 151-*n*. For example, the plurality of sensors 151-1 to 151-*n* included in the sensor unit 150 may include a motion sensor (not shown) for sensing a movement of the electronic device 100, as a sensor for user authentication, an iris recognition sensor (not shown) for recognizing the user's iris, a fingerprint recognition sensor (not shown) for recognizing a fingerprint, various sensors for sensing a surrounding environment (atmospheric pressure, temperature, humidity, illumination), a user gesture, etc.

The motion sensor may include at least one of an acceleration sensor, a geomagnetic sensor, and a gyro sensor. Various sensors included in the motion sensor may sense a three-dimensional (3D) movement of the electronic device 100 through one or a combination of two more of these.

The acceleration sensor is a sensor that measures a spatial motion of the electronic device 100. That is, the acceleration sensor means a sensor that senses a change in acceleration and/or a change in angular acceleration that occurs when the electronic device 100 moves. The acceleration sensor may sense acceleration in a 3-axial direction. Also, the acceleration sensor may sense an inclination of the electronic device 100.

The geomagnetic sensor is a sensor that measures an azimuth angle. That is, the geomagnetic sensor means a sensor that measures the azimuth angle by sensing a magnetic field formed in a north-south direction of the earth. The geomagnetic sensor may sense geomagnetism in the 3-axial direction. The north direction measured by the geomagnetic sensor may be a magnetic north. However, even if the geomagnetic sensor measures a direction of the magnetic north, a direction of a true north may be output through an internal computation.

The gyro sensor is an inertial sensor that measures a rotational angular velocity of the electronic device 100. That is, the gyro sensor means a sensor that may recognize a current direction by using the inertial force of a rotating object. The gyro sensor may measure the rotational angular velocity in a biaxial direction.

The motion sensor may sense a movement of the electronic device 100 and recognize a direction in which the electronic device 100 moves, the rotational angular velocity, and the like.

The sensor controller 152 is a configuration to collectively control the first to n-th sensors 151-1 to 151-n and serves as a sensor hurb. According to an embodiment, when the electronic device 100 operates in a sleep mode such as a standby mode or a power saving mode, power supplied to the controller 120 is limited, whereas a minimum amount of power may be supplied to the sensor unit 150 such that sensing is continuously performed through the sensor module even in a sleep mode state. That is, the sensor controller 152 may determine the context of the electronic device 100 based on the signals sensed by the sensors 151-1 to 151-n, and wake up the controller 120. While the controller 120 is being woken up, the sensor controller 152 may transmit a control signal to the removable HMD device 200 to sense the determined biological signal based on the determined context.

Meanwhile, the sensor unit 210 of the removable HMD device 200 may include a plurality of electrodes for sensing a biological signal of a user. The plurality of electrodes may include electrodes for sensing various biological signals such as an EMG signal, an EOG signal, an EEG signal, an ECG signal, a GSR signal, and a BIA signal, as described with reference to FIG. 2(a). The plurality of electrodes may be attached to a pad portion contacting the user's skin in the removable HMD device 200, and may be attached to an appropriate position according to a type of a biological signal to be sensed by each electrode on a pad.

The inputter 220 is a configuration to receive various inputs of a user, and may include a physically implemented button, a touch pad, or the like. For example, the inputter 220 may include a call button, a brightness control button, a volume control button, and the like, and may be associated with contents displayed on the electronic device 100 to receive an input of reproducing the contents, controlling a function of the contents, etc.

The communicator 230 is a configuration to perform wired/wireless communication with the electronic device 100. A structure and a function of the communicator 230 are redundant with those of the communication module included in the biological signal inputter 110 of the electronic device 100, and thus specific descriptions thereof are omitted.

The memory 240 is a configuration to store the biological signals sensed through the sensor unit 210. The processor 250 may control the memory 240 to store the biological signals sensed through the electrode in order to receive a plurality of biological signals through one electrode. The processor 250 may pass the stored biological signals to different filters and receive the biological signals corresponding to the respective filters.

The processor 250 is a configuration to generally control the removable HMD device 200. The processor 250 may remove noise by filtering the biological signal sensed through the sensor unit 210 and determine whether the user wears the removable HMD device 200 or whether the user properly wears the removable HMD device 200 based on characteristics of the sensed biological signal. Here, whether the user wears the HMD device 200 may be determined based on the above-described various types of biological signals, and is not particularly limited, but may be determined using an EMG signal.

When it is determined that the user wears the removable HMD device 200, the processor 250 may transmit a wakeup signal to the electronic device 100 in the sleep mode. Alternatively, when it is determined that a wearing state of the removable HMD device 200 of the user is defective, the processor 250 may transmit a signal informing that the user is not properly worn (in this case, the removable HMD device 200 may include an LED or a speaker that may provide a predetermined notice to the user) or transmit a signal to the electronic device 100 to output the signal informing that the user is not properly worn.

Also, the processor 250 may measure a signal quality of the biological signal sensed by the sensor unit 210 and may transmit a control signal for outputting a warning indicating that the signal quality sensed by a specific electrode is defective to the electronic device 100 based on the measured signal quality. Alternatively, the processor 250 may output the warning indicating that the signal quality sensed by the specific electrode is defective through the LED or the speaker provided to the removable HMD device 200.

Meanwhile, FIG. 2(b) illustrates the configuration and the operation of the electronic device 100 and the removable HMD device 200 when the electronic device 100 is implemented as the portable terminal device 100B. However, even when the electronic device 100 is implemented as the integrated HMD device 100A, those skilled in the art may easily change the design to apply the above-described operation.

For example, when the electronic device 100 is implemented as the integrated HMD device 100A, the configuration and the operation of the sensor unit 210 included in the removable HMD device 200 may be integrated into the sensor unit 150 of the electronic device 100, and the input/output module 220 will be included in the electronic device 100. The memory 240 may be integrated into the memory 140 of the electronic device 100 and the communication module included in the communicator 230 and the biological signal inputter 110 may be omitted. The operation of the processor 250 may be integrated into the operation of the processor 120 of the electronic device 100.

Figure 3:
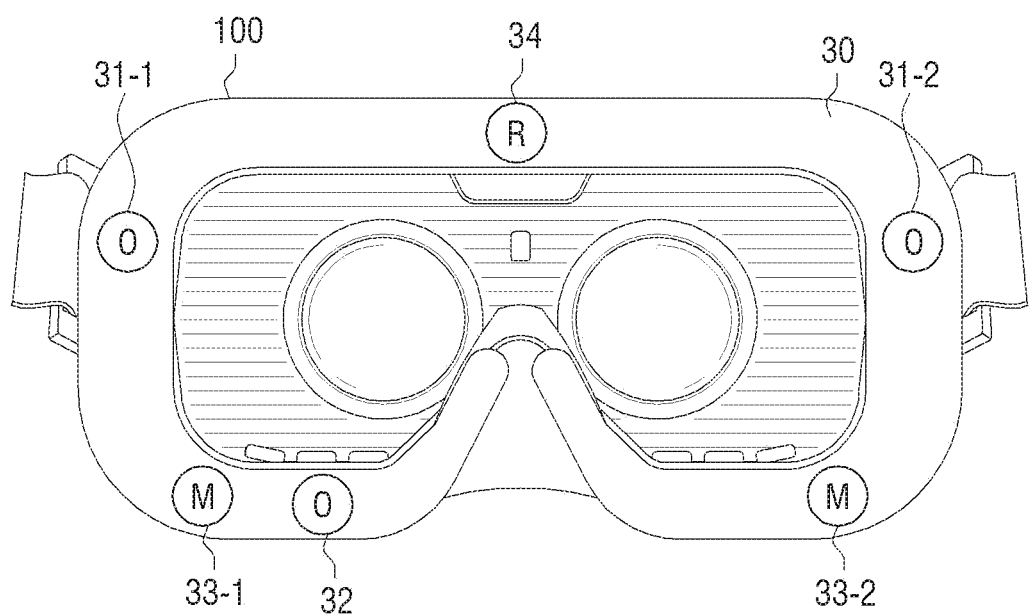
FIG. 3 is a diagram for explaining each electrode for sensing a biological signal according to an embodiment of the disclosure.

FIG. 3 is a diagram for explaining each electrode for sensing a biological signal according to an embodiment of the disclosure.

FIG. 3 is a front view of the electronic device 100 implemented as the integrated HMD device 100A or the removable HMD device 200 as viewed from a wearing side. As shown in FIG. 3, electrodes 31-1, 31-2, and 32 used to sense an EOG signal, electrodes 33-1 and 33-2 used to sense an EMG signal, and a reference electrode 34 may be provided on a pad 30 in contact with a wearer's face around the eye.

Basically, a pair of electrodes 31-1 and 31-2 may be attached to left and right sides of the eye to sense the EOG signal. Because each of the electrodes 31-1 and 31-2 calculates one electrode change, the pair of electrodes 31-1 and 31-2 may specify only left and right directions. Therefore, in order to set a direction of the eyeballs, it is necessary to set two directions of up and down and left and right. Therefore, at least one electrode 32 may be additionally provided on the pad 30 to be adhered to a lower end of the eye. Accordingly, the processor 120 may specify left and right directions of the eye using a pair of electrodes 31-1 and 31-2 attached to the left and right sides of the eye and specify up and down directions of the eye using a pair of electrodes 31-1 and 32 attached to the right side and lower end of the eye or a part of electrodes 31-2 and 32 attached to the left side and lower end of the eye. However, at least one electrode (not shown) may be additionally provided on a pad to be adhered to the upper end of the eye, and the processor 120 may specify the upper and lower directions of the eye using a pair of the electrode additionally provided on the upper end of the eye and the electrode 32 of the lower end of the eye.

On the other hand, a pair of electrodes 33-1 and 33-2 for sensing an EMG signal may be attached to the lower ends of both eyes. One electrode is attached to one muscle, and one value is calculated. The processor 120 may store the intensity of movement of each muscle for each muscle according to the intensity of electricity, and convert the magnitude of the sensed EMG signal.

The electrodes 33-1 and 33-2 for sensing the EMG signal may be provided annularly around the pad 30 and the electrodes 33-1 and 33-2 may sense a movement of muscles present in the entire face. In particular, the electrodes 33-1 and 33-2 for sensing the EMG signal may be provided on the pad 30 which adheres to the lower ends of both eyes so as to sense the movement of muscles around the eyes and around the cheekbones that mainly change a face shape, respectively.

Meanwhile, in order to sense the EMG signal, the reference electrode 34 may be additionally provided, and a differential value of a signal sensed through the both electrodes 33-1 and 33-2 and a signal sensed through the reference electrode 34 may be used as the EMG signal. The reference electrode 34 may be located on the pad 30 that adheres to an upper central region of both eyes. However, when a pair of electrodes for sensing the EMG signal is additionally provided and a bi-polar for sensing the EMG signal using a potential difference of an adjacent electrode pair is used, the reference electrode 34 may not be required.

Figure 4:
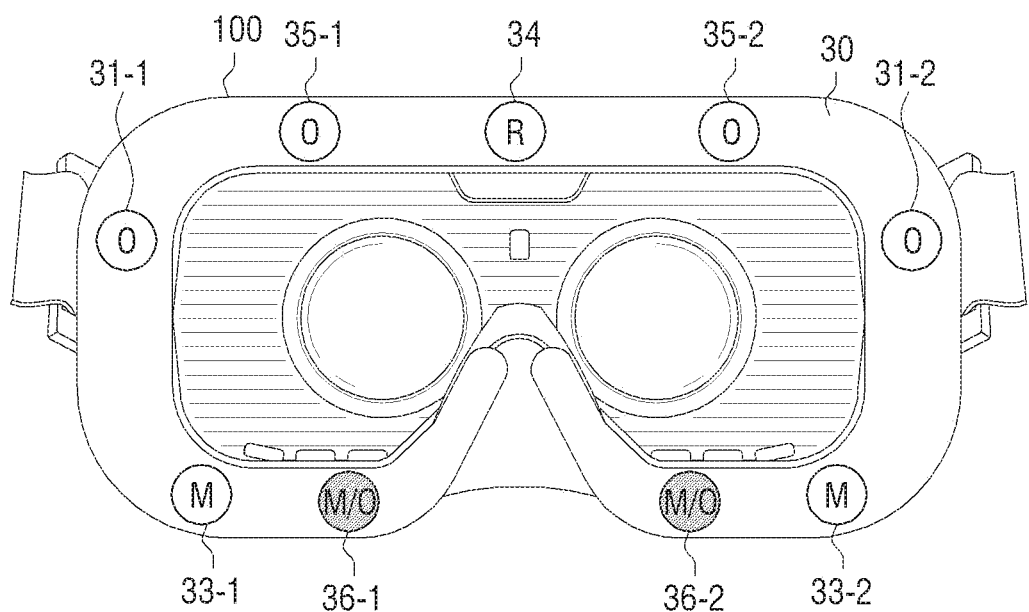
FIG. 4 is a diagram for explaining common electrodes for sensing a biological signal according to another embodiment of the disclosure.

FIG. 4 is a diagram for explaining common electrodes for sensing a biological signal according to another embodiment of the disclosure.

An electrode according to an embodiment of the disclosure may further include the common electrodes 36-1 and 36-2 used for sensing any one biological signal determined based on a context of the electronic device 100 of an EOG signal and an EMG signal. When a type of the biological signal to be sensed is determined, the processor 120 may select a channel corresponding to the common electrodes 36-1 and 36-2 as a channel to receive the determined biological signal, and based on characteristics of the determined biological signal, set a state of the channel corresponding to the common electrodes 36-1 and 36-2. Specifically, the processor 120 may adjust a sampling rate and an ADC resolution for sensing the biological signal according to the determined biological signal and pass a signal sensed from the common electrodes 36-1 and 36-2 through any one of a filter for filtering the EOG signal and a filter for filtering the EMG signal to separate the EOG signal and the EMG signal.

The electronic device 100 implemented as the integrated HMD device 100A or the removable HMD device 200 may include at least one common electrode. FIG. 4 illustrates an example in which a pair of common electrodes 36-1 and 36-2 is provided at a position adhered to lower ends of both eyes of the pad 30.

Each pair of electrodes 31-1, 31-2, 35-1, and 35-2 for sensing the EOG signal may be provided on left and right sides of both eyes and on upper ends of both eyes.

The common electrodes 36-1 and 36-2 of FIG. 4 may be used as electrodes for sensing the EMG signal or electrodes for sensing the EOG signal according to the context of the electronic device 100. For example, when the context of the electronic device 100 is determined as 'navigating', the processor 120 may determine the type of the biological signal to be input as the EOG signal. At this time, the processor 120 may determine left and right directions of the eye by using the pair of common electrodes 36-1 and 36-2 and determine up and downs directions of the eye by using any one of the pair of common electrodes 36-1 and 36-2 and any one of the electrodes 35-1 and 35-2 of upper ends of both eyes.

Also, when the context of the electronic device 100 is determined as 'user authentication', the processor 120 may determine the type of the biological signal to be input as the EMG signal. At this time, the processor 120 may determine a movement of the facial muscle by using the pair of the common electrodes 36-1 and 36-2 and the reference electrode 34.

That is, the common electrodes 36-1 and 36-2 are electrodes commonly used to sense the EOG signal or sense the EMG signal according to the context of the electronic device 100. In accordance with the context, the common electrodes 36-1 and 36-2 may be used to sense the biological signal, together with the other electrodes 31-1, 31-2, 33-1, 33-2, 34, 35-1 and 35-2.

Meanwhile, the processor 120 may set a state of a channel corresponding to the common electrodes 36-1 and 36-2 according to the characteristics of the biological signal. Specifically, the processor 120 may set the sampling rate, cutoff frequency, ADC resolution, and the like of the channel corresponding to the common electrodes 36-1 and 36-2 in accordance with the characteristics of the determined biological signal, as described above, and receive only an electrical signal with respect to the determined biological signal.

A specific input process of the biological signal will be described in detail with reference to FIG. 5.

Figure 5:
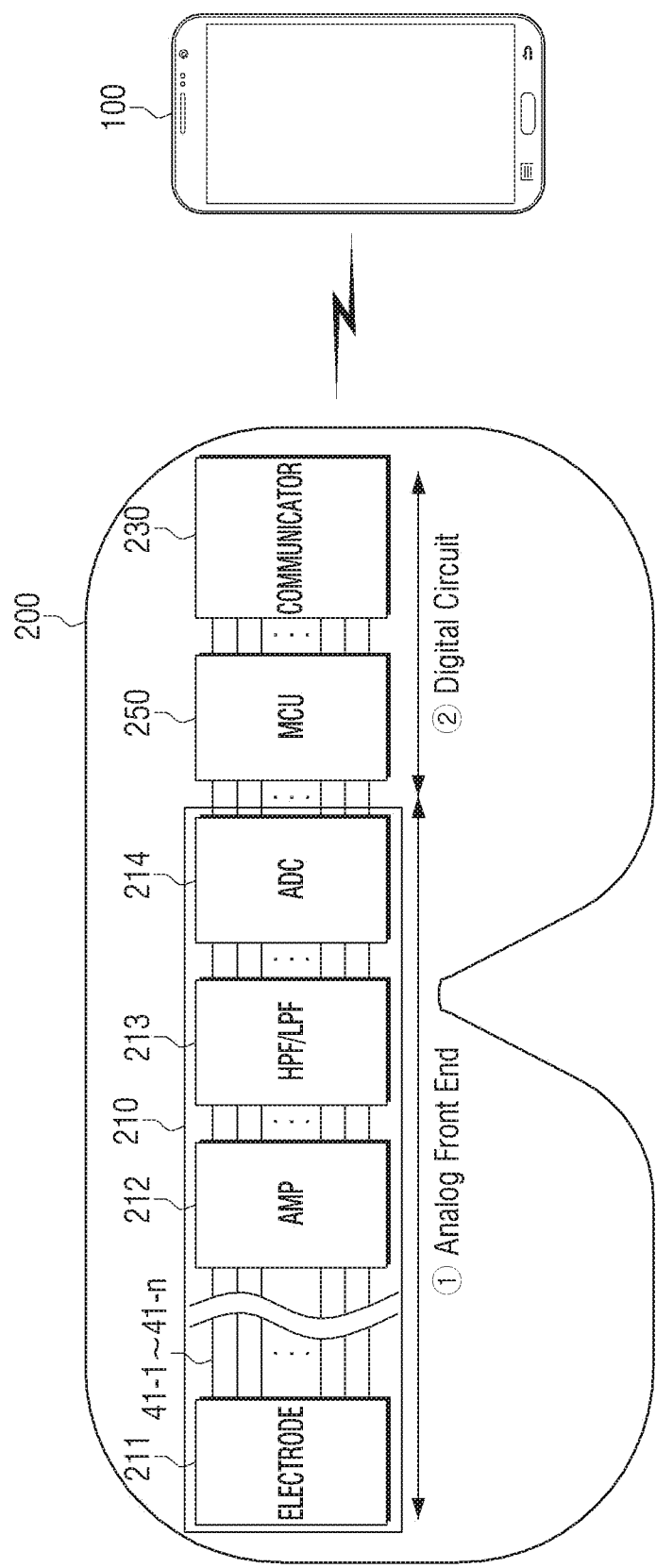
FIG. 5 is a diagram for explaining each signal flow process in an electronic device according to an embodiment of the disclosure.

FIG. 5 is a diagram for explaining each signal flow process in an electronic device according to an embodiment of the disclosure.

The embodiment shown in FIG. 5 shows a process of inputting and processing biological signals sensed from a plurality of electrodes 211 provided in the removable HMD device 200 to the electronic device 100 mounted on the removable HMD device 200.

The biological signals sensed from the plurality of electrodes 211 are transmitted to the electronic device 100 through channels 41-1 to 41-$n$ corresponding to the respective electrodes 211. An EMG signal is converted into a digital signal via an analog-to-digital converter (ADC) 214. Accordingly, the removable HMD device 200 includes ① an analog front end for processing an analog signal from the ADC 214 and ② a digital circuit for processing a digital signal converted from an analog signal.

① The analog front end includes an operation of the sensor unit 210. Specifically, the analog front end includes operations of the electrodes 211 for sensing the biological signals, an amplifier AMP 212 for amplifying the sensed biological signals, a HPF (High Pass Filter)/LPF (Low Pass Filter) 213 for removing noise of the amplified biological signals, and the ADC 214 for converting the biological signals from which noise is removed into digital signals. ② The digital circuit is a configuration for processing the biological signals converted into the digital signals, and includes a processor 250 for performing filtering through the HPF (High Pass Filter)/LPF (Low Pass Filter) 213 and a communicator 230 for transmitting the filtered digital biological signals to the electronic device 100. In the embodiment shown in FIG. 5, the processor 250 is implemented as an MCU (Micro Controller Unit).

For example, when the biological signal is the EMG signal, in FIG. 3, a potential difference between a voltage of the EMG signal sensed by a user's right facial muscle and a reference voltage sensed through the reference electrode 34 may be detected through the electrodes 33-1 and 33-2 used for sensing the EMG signal. The EMG signal including the detected potential difference may be amplified through the amplifier AMP 212 provided in the removable HMD device 200. Noise of the amplified EMG signal may be removed through the HPF/LPF 213 provided in the removable HMD device 200. Here, the HPF may remove noise of a DC component from the amplified EMG signal, and the LPF may remove noise other than the DC component from the amplified EMG signal.

The EMG signal from which noise is removed is converted into a digital signal via the ADC 214, after being subjected to high-pass and low-pass filtering in the MCU 250, is transmitted to the communicator 230, and is transmitted to the communicatively connected electronic device 100 in real time.

The processor 120 may select a channel corresponding to a target electrode or a common electrode from among the plurality of channels 41-1 to 41-$n$ as a channel to receive the determined biological signal and, based on characteristics of the determined biological signal, set a state of the channel corresponding to the target electrode or the common electrode.

Specifically, when the biological signal to be input is determined based on a context of the electronic device 100, the processor 120 may transmit information about the determined biological signal to the removable HMD device 100 through a communication module included in the biological signal inputter 110. At this time, a communication method of the biological signal inputter 110 of the electronic device 100 and the communicator 230 of the removable HMD device 200 may be performed by wired or wirelessly.

In an embodiment in which communication between the biological signal inputter 110 of the electronic device 100 and the communicator 230 of the removable HMD device 200 is performed wirelessly, at least one method of NFC, Wi-Fi, Wi-Fi Direct, Zigbee, and Bluetooth may be implemented to perform communication and other various wireless communication methods may be implemented to perform communication.

In an embodiment in which communication between the biological signal inputter 110 of the electronic device 100 and the communicator 230 of the removable HMD device 200 is performed by wired, various methods including a method of Universal Asynchronous Receiver/Transmitter (UART) may be implemented to perform communication.

When the communicator 230 of the removable HMD device 200 receives the information about the biological signal determined according to the context from the biological signal inputter 110 of the electronic device 100, the MCU 250 determines whether a type of the determined biological signal and selects a channel corresponding to the target electrode for sensing the corresponding biological signal according to the type of the determined biological signal. The MCU 250 may then control the HPF/LPF 213, the ADC 214, and the like such that at least one of a sampling rate, an ADC resolution, and a cutoff frequency with respect to the biological signal received through the selected channel is set according to characteristics of the determined biological signal. That is, the MCU 250 may control the sensor unit 210 to perform software filtering.

The ADC 214 may transmit a bioelectrical signal converted into the digital signal to the MCU 250 only through the selected channel according to the type of the determined biological signal. Accordingly, the MCU 250 may selectively receive the sensed biological signal only through a specific channel according to the context, without receiving the sensed biological signal through all the channels. That is, the MCU 250 may control the ADC 214 to ignore signals received through channels other than the selected channel according to the context without processing the signals.

For example, when the biological signal determined according to the context is an EOG signal, the processor 120 may control the biological signal inputter 110 to transmit information that the determined biological signal is the EOG signal to the communicator 230. When the communicator 230 receives the information, the MCU 250 may select a channel corresponding to the target electrode for sensing the EOG signal, and control the ADC 214 to transmit only the EOG signal transmitted through the selected channel to the MCU 250. Also, the MCU 250 may filter the remaining signals excluding the EOG signal from the biological signal transmitted through the selected channel by setting the sampling rate and the cutoff frequency of the biological signal to be sensed to correspond to an amplitude and a period of the EOG signal.

In another embodiment, the MCU 250 may control power supplied to any one of the AMP 212, the HPF/LPF 213, and the ADC 214 such that the biological signal is not transmitted through channels other than the selected channel That is, the AMP 212, the HPF/LPF 213, and the ADC 214 may be powered on each channel.

That is, when the biological signal to be input is determined, the MCU 250 may activate only the channel corresponding to the electrode for sensing the determined biological signal, and deactivate channels other than the channel corresponding to the electrode for sensing the determined biological signal, thereby reducing power waste consumed by unused electrodes.

Meanwhile, according to an embodiment of the disclosure, the MCU 250 may measure an input state of the biological signal and may change a channel to which the biological signal is to be input according to the measured input state of the biological signal. Specifically, the MCU 250 may determine a contact state or an impedance value of the target electrode with respect to a site where the biological signal is to be sensed, and when it is determined that the contact state of the target electrode is defective (for example, when magnitude of the biological signal to be sensed is extremely greater than a predetermined value) or when the impedance value is measured to be higher than the predetermined value (for example, when makeup is heavy on the user's face), may change the target electrode to another electrode for measuring the same type of a biological signal. Even when a plurality of reference electrodes are present, the MCU 250 may change the reference electrode based on a contact state of the reference electrode or an impedance value by a BIA signal.

For example, referring to FIG. 4, while the pair of electrodes 33-1 and 33-2 for sensing the EMG signal under the eye may be set as a target electrode for sensing the EMG signal, when an input state of the EMG signal measured through any one of the electrodes 33-1 and 33-2 is in a defective state, the MCU 250 may change the target electrode to receive the EMG signal from any one of the common electrodes 36-1 and 36-2 close to a defective electrode instead of the defective electrode. For example, according to the input state of the EMG signal, an electrode of a lower end of the left eye in the pair of electrodes 33-1 and 33-2 and a common electrode of a lower end of the right eye in the pair of common electrodes 36-1 and 36-2 may be paired to receive the EMG signal.

Meanwhile, the input state of the biological signal may be measured not only by using an impedance value of the biological signal but also by using a signal-to-noise ratio (SNR), a common mode rejection ratio (CMRR), etc.

Meanwhile, as described above, the embodiment shown in FIG. 5 shows the electronic device 100 and the removable HMD device 200, in the example in which the electronic device 100 implemented as the portable terminal device 100B is detached and implemented in the removable HMD device 200, the above-described disclosure describes the operation of each of the electronic device 100 and the removable HMD device 200. However, even when the electronic device 100 is implemented as the integrated HMD device 100A, the technical idea shown in FIG. 5 may be applied in the same manner. In this case, the operation of the MCU 250 of the removable HMD device 200 of FIG. 5 may be performed by the processor 120 of the electronic device 100 and the communicator 230 of the removable HMD device 200 for communicating with the electronic device 100 may be omitted.

Hereinafter, an embodiment in which the electronic device 100 of the disclosure is assumed to be an integrated HMD device will be described, unless otherwise specified. However, the technical idea of the disclosure described below may also be applied to the case where the electronic device 100 of the disclosure is implemented and embodied as a removable HMD device provided with a sensor and a detached portable terminal device.

Figure 6:
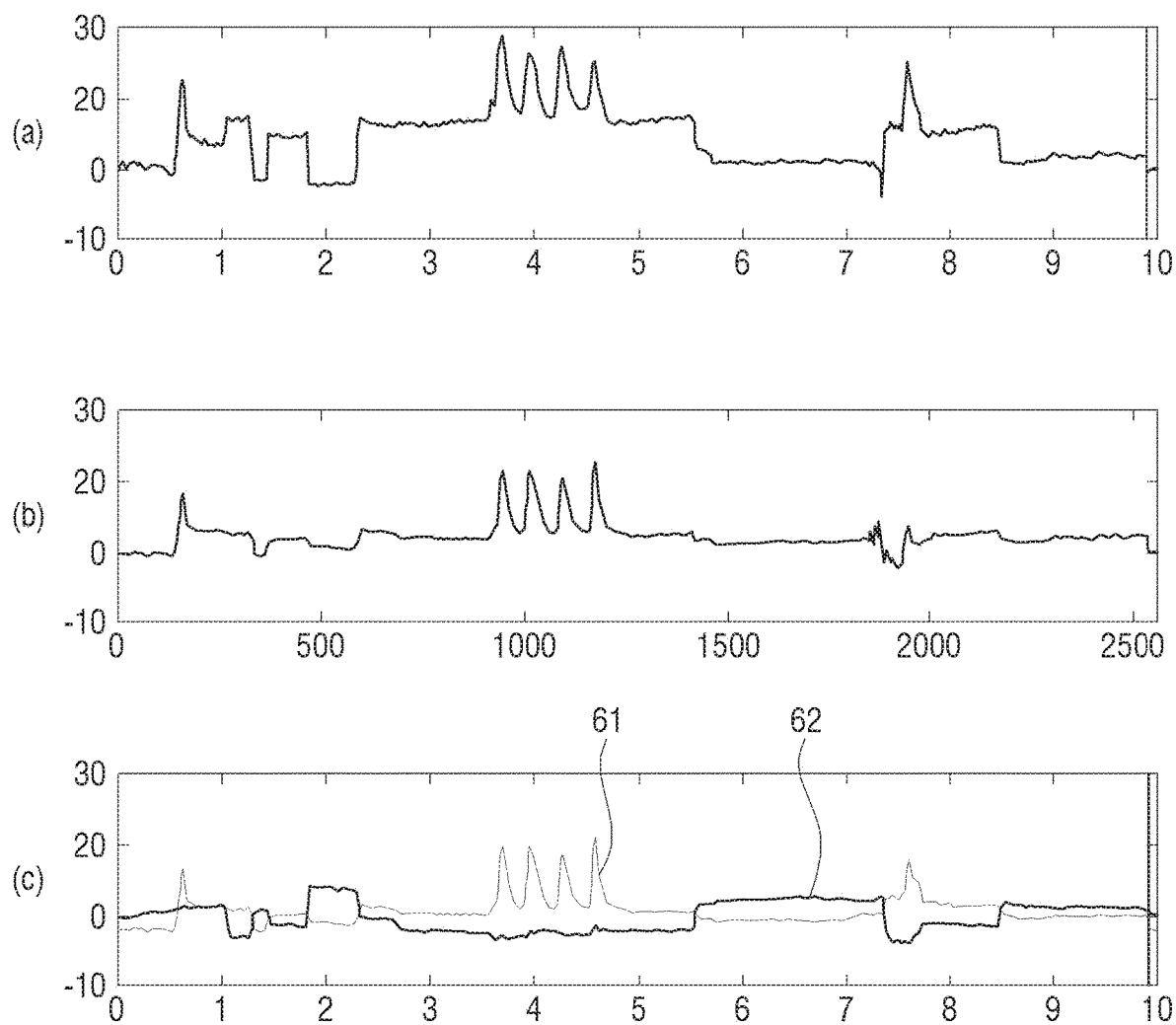
FIG. 6 is a diagram for illustrating an EOG signal and an EMG signal according to an embodiment of the disclosure.

FIG. 6 is a diagram for illustrating an EOG signal and an EMG signal according to an embodiment of the disclosure.

FIG. 6(*a*) shows a waveform of the EOG signal sensed in an electrode or a common electrode used for sensing the EOG signal. FIG. 6(*b*) shows a waveform of the EMG signal sensed in an electrode or a common electrode used for sensing the EMG signal.

Because electrodes attached to the electronic device 100 are all located close to the eyes, the EMG signal shown in FIG. 6(*a*) may include the EMG signal, and the EMG signal shown in FIG. 6(*b*) may include the EOG signal.

At this time, the processor 120 may derive a waveform 62 of the EMG signal as shown in FIG. 6(*c*) by subtracting the signal of (b) from the signal of (a). Meanwhile, the processor 120 may derive a waveform 61 of the EOG signal by subtracting the derived waveform 62 of the EMG signal from the signal of (a).

Figure 7:
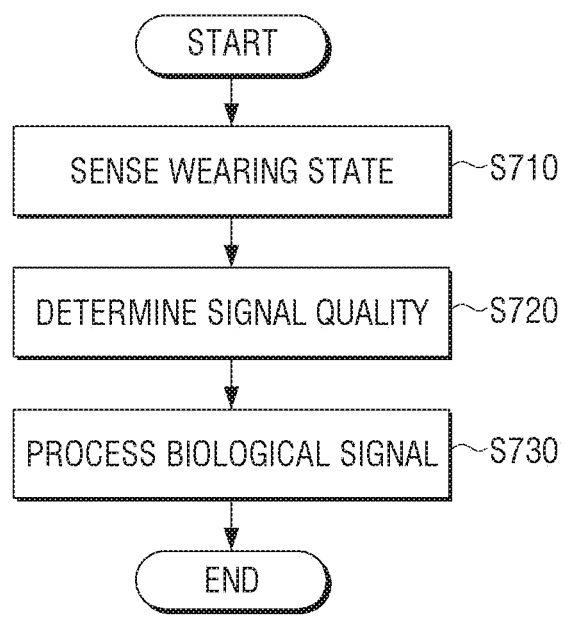
FIG. 7 is a brief flowchart explaining a process of operating an electronic device according to an embodiment of the disclosure.

FIG. 7 is a flowchart briefly explaining a process of operating the electronic device according to an embodiment of the disclosure.

An operation of the electronic device 100 may be largely classified into three steps. Step S710 of sensing a wearing state of the electronic device 100, step S720 of determining the signal quality of the sensed biological signal, and step S730 of processing the sensed biological signal to perform an operation according to a biological change of a user.

In step S710, it is determined whether the electronic device 100 is worn by the user and whether the wearing state is defective. The wearing state of the electronic device 100 may be determined from a biological signal that is sensed through an electrode of the electronic device 100 and input to the biological signal inputter 110, and in particular may be determined using a BIA signal in the electrode. In order to sense the wearing state of the electronic device 100, a minimum amount of power for sensing the biological signal may be supplied to the biological signal inputter 110. That is, the electronic device 100 may operate in a sleep mode, and when the biological signal is sensed, may be switched to a normal mode (a state in which power is normally supplied).

In another embodiment, in a state where the electronic device 100 is in the sleep mode, when a minimum amount of power is supplied to the sensor unit 150 and a movement of the electronic device 100 is sensed through the sensor unit 150, power may be supplied to the biological signal inputter 110 to receive the biological signal.

On the other hand, the electronic device 100 may determine whether the electronic device 100 is worn by the user using characteristics of the biological signal sensed from an electrode of a specific position. The characteristics of a specific biological signal sensed from the electrode of the specific position when the user wears the electronic device 100 properly may be stored in the memory 140. The characteristics of the specific biological signal stored in the memory 140 and characteristics of a currently sensed specific biological signal may be compared to determine whether the electronic device 100 is worn and whether the wearing state of the electronic device 100 is defective.

When the wearing state of the electronic device 100 is defective, the electronic device 100 may output a warning message or a warning alarm through the outputter 130 to properly wear the electronic device 100.

When the electronic device 100 is properly worn, the quality of the biological signal input through the biological signal inputter 110 is determined in step S720. A state of a channel corresponding to each of a plurality of electrodes may be activated such that all of the biological signals sensed from the plurality of electrodes included in the electronic device 100 may be received. Accordingly, the electronic device 100 may determine all of the quality of the signals sensed from the plurality of electrodes.

The electronic device 100 may compare the signals sensed from the plurality of electrodes with a normal signal that is normally sensed and, when the signal quality of the specific electrode is determined to be defective, output a warning to replace the electrode or sense the biological signal through another electrode around the electrode of which signal quality is determined to be defective. In this case, the signal quality may be determined through an analysis of at least one of a signal-to-noise ratio (SNR), magnitude of an amplitude of a signal current in a time domain, and a range of the signal current in a frequency domain.

On the other hand, in step S730, the biological signal to be input is determined based on a current context of the electronic device 100, and the determined biological signal is received and processed. Specifically, the electronic device 100 sets a state of a channel corresponding to an electrode for sensing the determined biological signal according to the determined biological signal, and determines a biological change using the biological signal input according to the set state of the channel Various operations may be performed according to the determined biological change. The operations performed according to the biological change will be described in detail in the embodiments shown in FIGS. 9 to 12.

Figure 8:
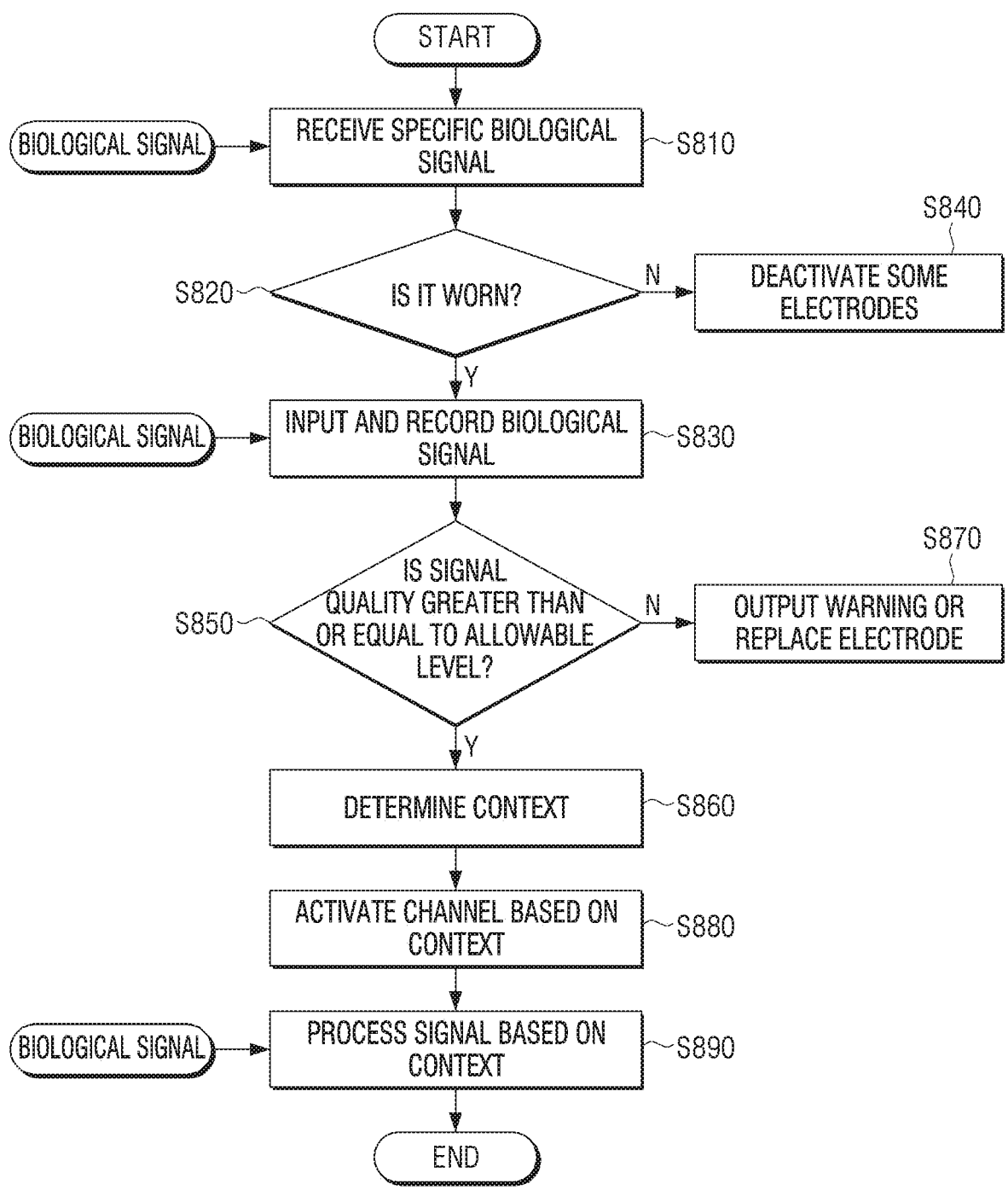
FIG. 8 is a detailed flowchart explaining a process of operating an electronic device according to an embodiment of the disclosure.

FIG. 8 is a detailed flowchart explaining a process of operating the electronic device 100 according to an embodiment of the disclosure.

First, in order to determine whether the electronic device 100 is worn, the electronic device 100 senses and receives a specific biological signal through an electrode for sensing a wearing state of the electronic device 100 (S810). Here, the biological signal to be sensed to determine whether the electronic device 100 is worn may be an EMG signal, but it is not necessarily limited thereto, and it may be determined whether the electronic device 100 is worn by various biological signals. At this time, when the electronic device 100 is lifted by a user, a movement of the electronic device 100 may be sensed by a movement sensor 160 included in the electronic device 100, and a channel corresponding to an electrode capable of sensing the EMG signal for determining whether the electronic device 100 is worn may be activated.

When it is determined that the electronic device 100 is worn (S820: Y), the electronic device 100 receives the biological signal sensed from the electrode and records the inputted biological signal (S830). When it is determined that the electronic device 100 is not worn (S820: N), a channel corresponding to some electrodes or all the electrodes may be deactivated, thereby reducing power consumption due to activation of the electrodes.

Further, the electronic device 100 may output a result of determination on the wearing state of the electronic device 100. When the wearing state is defective, the electronic device 100 may output a message or guidance speech indicating that the electronic device 100 is not properly worn. When the wearing state is good, the electronic device 100 may output a message or guidance speech indicating that the electronic device 100 is properly worn.

Thereafter, the electronic device 100 measures the quality of the input biological signal and determines whether the measured quality of the biological signal is greater than or equal to an allowable level (S850). At this time, the measured quality of the biological signal may be measured not only by using an impedance of the biological signal, but also by using the SNR, CMRR, etc. When a measured value is greater than or equal to a predetermined threshold value, the quality may be determined to be defective. Likewise, when the measured value is less than the predetermined threshold value, the quality may be determined to be good.

When it is determined that the measured quality of the biological signal is defective (S850: N), the electronic device 100 may output a warning message or a warning sound indicating that the electrode is defective through the outputter 130 or may replace the corresponding defective electrode whose measured quality of the biological signal is defective with another electrode nearby to sense the biological signal.

When it is determined that the measured quality of the biological signal is good (S850: Y), a context of the electronic device 100 is determined (S860). The electronic device 100 determines a biological signal to be input based on the determined context, and activates a channel corresponding to an electrode for sensing the determined biological signal (S880). The electronic device 100 may process the biological signal by setting a state of the channel corresponding to the electrode for sensing the determined biological signal to a state suitable for receiving the determined biological signal based on the context (S890). At this time, the electronic device 100 may set a sampling rate of the channel corresponding to the electrode for sensing the determined biological signal, an ADC resolution, and a cut-off frequency.

FIGS. 9 to 12 are diagrams for explaining operations of the electronic device 100 according to various contexts, according to an embodiment of the disclosure.

Figure 9:
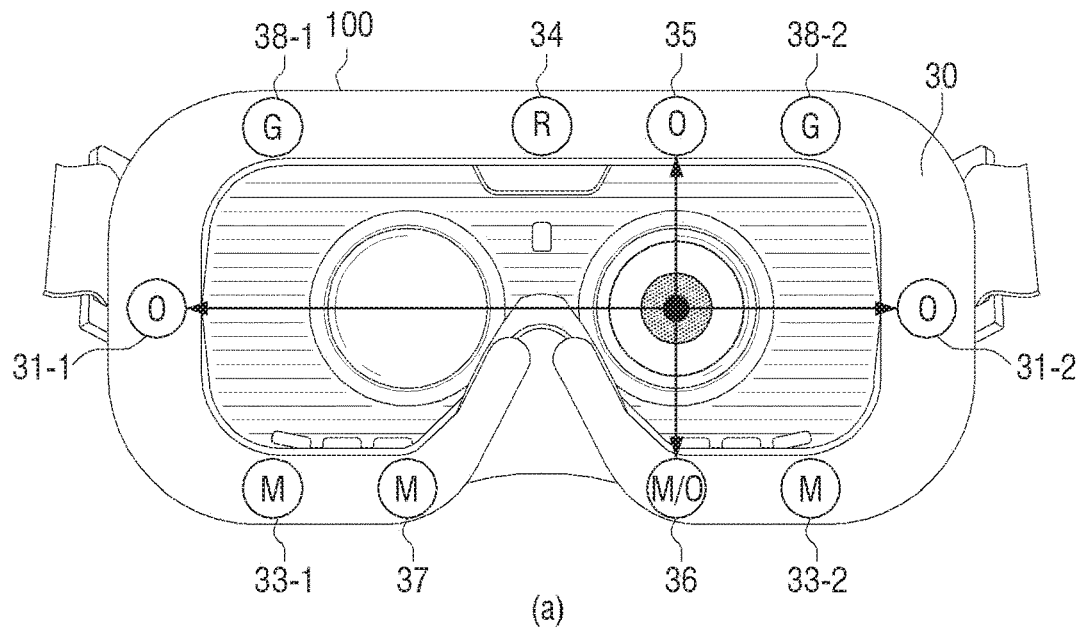
FIGS. 9 to 12 are diagrams for explaining operations of an electronic device according to various contexts, according to an embodiment of the disclosure.
Figure 9:
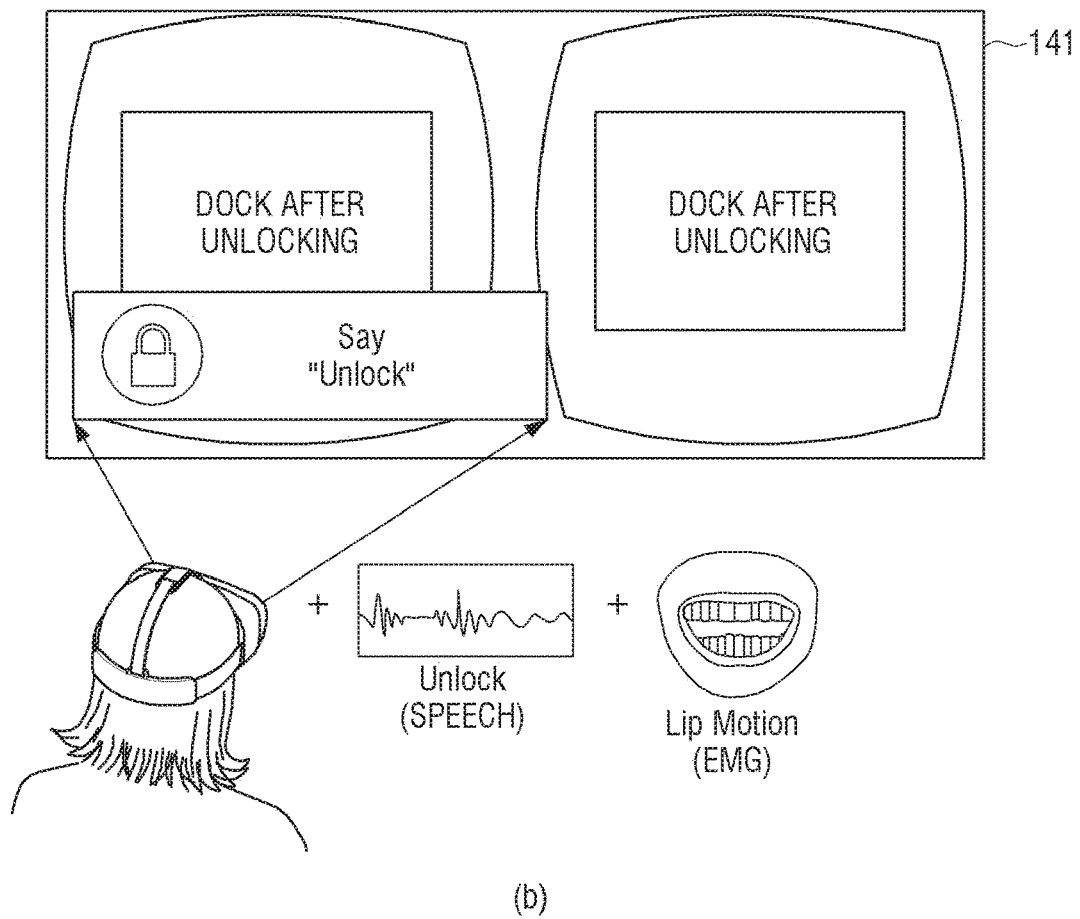

FIG. 9 shows a case where a context of the electronic device 100 is an environment in which a screen for user authentication is displayed.

According to an embodiment shown in FIG. 9(*a*), the electrodes 31-1, 31-2, and 35 for sensing an EOG signal, the electrodes 33-1, 33-2, and 37 for sensing an EMG signal, the common electrode 36 for sensing both the EOG signal and the EMG signal, the reference electrode 34 and ground electrodes 38-1 and 38-2 may be provided on the pad 30 that is in contact with a face of the electronic device 100.

A pair of electrodes 31-1 and 31-2, which are respectively attached around a left temple and a right temple of the both eyes, may sense a movement of the eyeball in a left and right direction. The electrodes 35 and 36, which are respectively attached to upper and lower ends of the right eye, may sense a movement of the eyeball in a up and down direction. The common electrode 36 of the lower end of the right eye may sense both the EMG signal and the EOG signal but the processor 120 may perform filtering to filter the EMG signal or the EOG signal based on the context of the electronic device 100 to selectively receive the EMG signal or the EOG signal.

According to an embodiment shown in FIG. 9(*b*), in case where the electronic device 100 is in a lock state, when a user wears the electronic device 100 for the first time, a message "Dock after unlocking" is output. In the related art, there has been an inconvenience that the user must unlock the electronic device 100 and wear the electronic device 100 again according to such a message. However, in the disclosure, the user may unlock the electronic device 100 by using a biological signal of the user without taking off the electronic device 100.

Specifically, the EOG signal and the EMG signal sensed from a plurality of electrodes, and a speech signal input through a microphone (not shown) included in the electronic device 100 may be used to unlock the electronic device 100. For example, as shown in FIG. 9(*b*), the display 131 may display a message "say unlock" on one side of the screen requesting unlocking. At this time, the processor 120 may control to unlock when the user utters "unlock" while looking at the message "say unlock".

Specifically, when a screen (for example, a lock screen, a payment screen, or the like) requesting user authentication is displayed on the display 131, the processor 120 may determine an EOG signal for sensing user's eyes and an EMG signal for sensing a mouth shape of the user as a biological signal to be input based on the context (user authentication) of the electronic device 100. The processor 120 may activate a channel corresponding to the electrodes 31-1, 31-2, 35 and 36 for receiving the EOG signal and a channel corresponding to the electrodes 33-1, 33-2, and 37 for receiving the EMG signal according to the determined biological signal and receive the biological signal through the activated channels. The common electrode 36 may be further included as the electrode for receiving the EMG signal. At this time, the EOG signal and the EMG signal sensed through the common electrode 36 may be separated from each other through filtering.

Thereafter, the processor 120 may unlock the screen when all of a condition (condition 1) in which the user's eyes face at the message "say unlock" displayed on one side of the screen through the EOG signal sensed from the electrodes 31-1, 31-2, 35 and 36 around both eyes, a condition (condition 2) in which the speech signal sensed through the microphone is recognized as "unlock", and a condition (condition 3) in which the mouth shape of the user matches a mouth shape that utters "unlock" through the EMG signal sensed from the electrodes 33-1, 33-2, 36 and 37 around the mouth are satisfied.

Accordingly, the screen may be unlocked only when the already authenticated user wears the electronic device 100 and directly utters "unlock". Accordingly, when the user reproduces a recorded speech without directly uttering, security may be enhanced by preventing the screen from being unlocked. Also, by sensing the EMG signal in a noisy environment and determining whether the user has uttered "unlock", the electronic device 100 may be utilized as auxiliary means of the microphone for recognizing the user.

Figure 10:
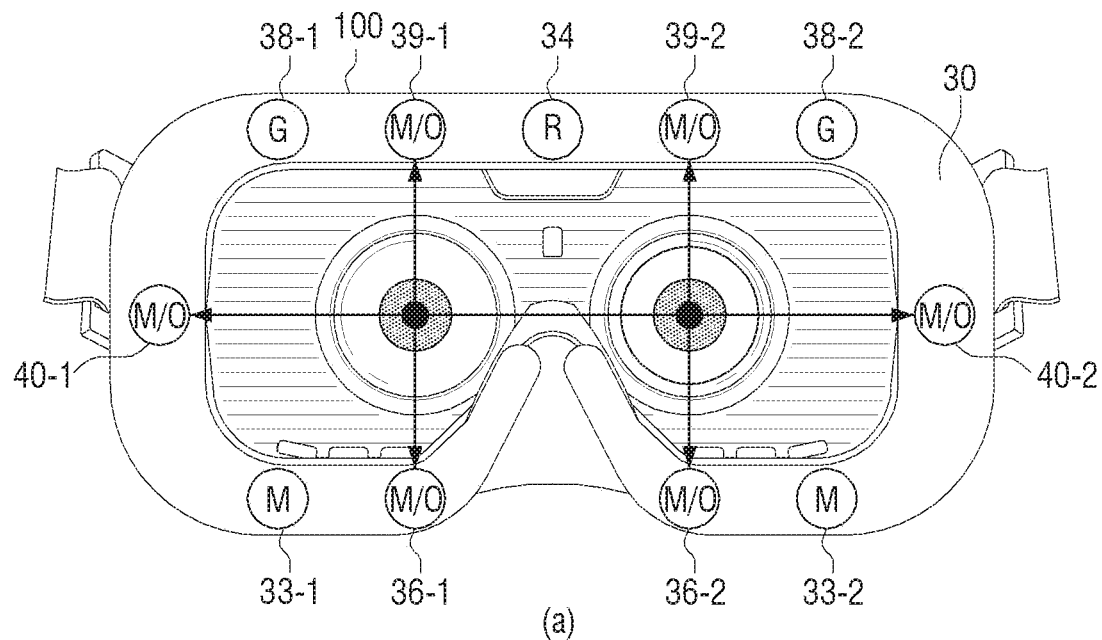
Figure 10:
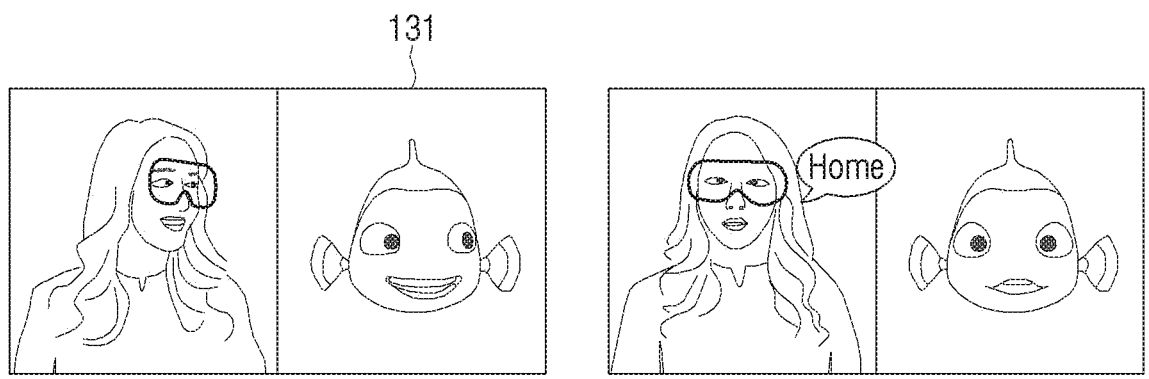
Figure 10:
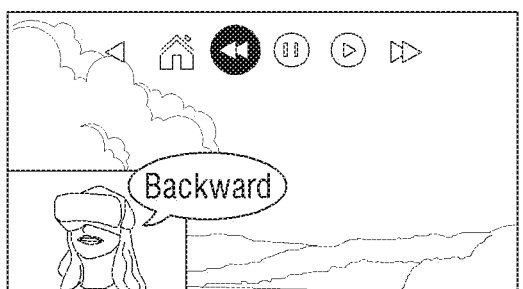

FIG. 10 shows a case where the context of the electronic device 100 is an environment in which a screen for recognizing a facial expression is displayed.

According to the embodiment shown in FIG. 10(*a*), the electrodes 33-1 and 33-2 for sensing the EMG signal, common electrodes 36-1, 36-2, 39-1, 39-2, 40-1, and 40-2 for sensing both the EOG signal and the EMG signal, the reference electrode 34 and ground electrode 38 may be provided on the pad 30 that is in contact with the face of the electronic device 100.

In the screen for recognizing the facial expression, a need to accurately recognize the user's facial expression increases. Therefore, a large number of electrodes for sensing the EMG signal are needed in each part of the face. Because recognition of the facial expression includes recognition of the user's eyes, the common electrodes 36-1, 36-2, 39-1, 39-2, 40-1, and 40-2 for sensing both the EOG signal and the EMG signal may be provided on a position of the pad 30 attached to the eyes.

FIG. 10(*b*) shows a screen on which a facial expression recognition application for displaying a fish tracking a user's facial expression is displayed by recognizing a change of the user's facial expression (an eyes direction and a mouth motion). According to the change of the user's facial expression, an expression of the fish including a pupil position or a mouth shape of the fish may be changed. A change of the user's eyes may be sensed based on a movement of one eye or a movement of both eyes. When the change of the user's eyes is sensed according to the movement of one eye, the common electrodes 40-1 and 40-2 around the temple in the both eyes and the common electrodes 36-1 and 39-2 or 36-2 and 39-2 attached to the upper and lower sides of any one eye of both eyes may be used to sense the change of the user's eyes.

Also, a shortcut instruction based on the mouth shape of the user may be previously stored, and a shortcut instruction corresponding to the mouth shape of the user recognized through the electrodes 33-1, 33-2, 36-1, and 36-2 for sensing the EMG signal may be executed. That is, the user may use the electronic device 100 in a hands-free manner. Here, the shortcut command may include "Home" for displaying a home screen (a content selection screen displayed basically when an O/S of the electronic device 100 or a specific application is executed), "Back" for returning to a previous screen, "Select" for selecting a specific menu or contents, "Volume" for adjusting the volume, and the like. For example, the processor 120 may recognize a mouth shape in which a user pronounces "Home" to display the home screen.

When a screen for performing recognition of the facial expression is displayed on the display 131 (for example, a facial expression recognition application is executed, etc.), the processor 120 may determine the EMG signal for recognizing the user's facial expression and the EOG signal for sensing the user's eyes as the biological signal to be input based on the context (recognition of the facial expression) of the electronic device 100. The processor 120 may activate a channel corresponding to an electrode for receiving the EOG signal and the EMG signal according to the determined biological signal. In the embodiment shown in FIG. 10(*a*), the common electrodes 36-1, 36-2, 39-1, 39-2, 40-1, and 40-2 capable of sensing both the EOG signal and the EMG signal as well as an electrode for sensing a single kind of biological signal, such as the electrodes 33-1 and 33-2 for sensing the EMG signal, may be utilized.

On the other hand, the processor 120 may use a motion detection sensor included in the electronic device 100 to track the user's head. When the user's head rotates in a left direction, the EOG signal sensed from a movement of a left eyeball is larger than the EOG signal sensed from a movement of a right eyeball, and when the user's head rotates in a right direction, the EOG signal sensed from the movement of the right eyeball is larger than the EOG signal sensed from the movement of the left eyeball.

Accordingly, the processor 120 may selectively receive either a safety signal corresponding to the left eye or a safety signal corresponding to the right eye according to a rotation direction of the user's head using the motion detection sensor. For example, when the user's head rotates to the left or the right, the processor 120 may selectively activate a channel corresponding to the electrodes 36-1, 39-1, and 40-1 for sensing the EOG signal of the left eye or a channel corresponding to the electrodes 36-2, 39-2, and 40-2 for sensing the EOG signal of the right eye to determine a movement of the user's eyes by using only the EOG signal of one eye.

Figure 11:
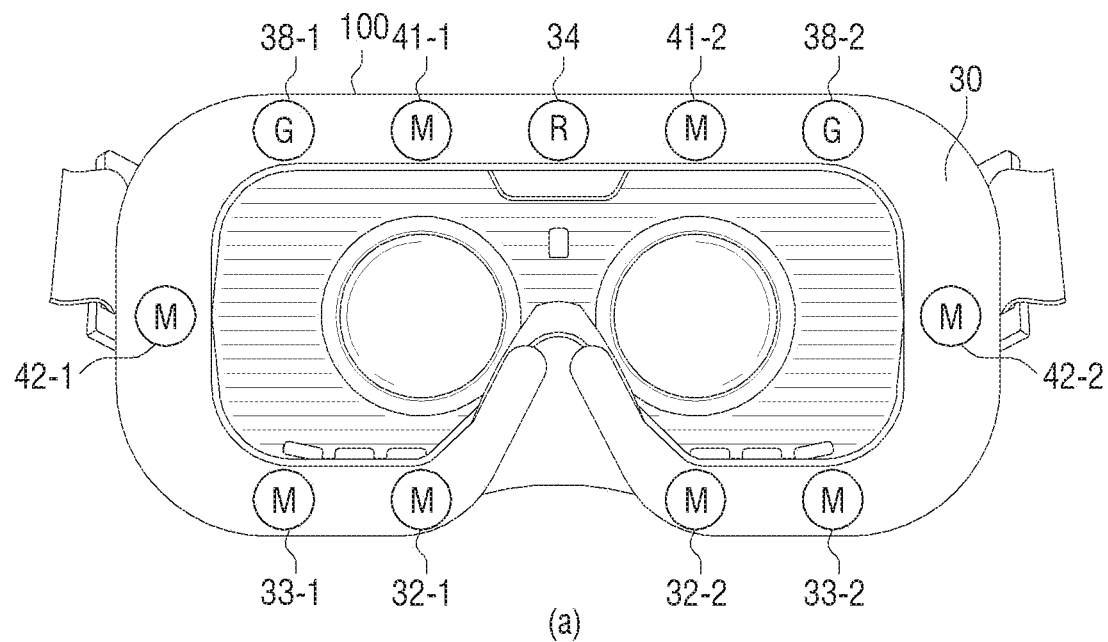
Figure 11:
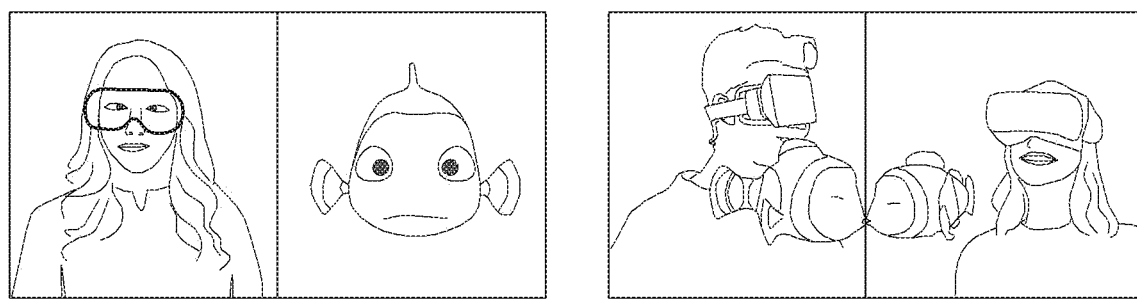

Meanwhile, according to an embodiment shown in FIG. 11(*a*), the electrodes 32-1, 32-2, 33-1, 33-2, 41-1, 41-2, 42-1, and 42-2 for sensing the EMG signal, the reference electrode 34, and the ground electrode 38 may be provided on the pad 30 that is in contact with the face of the electronic device 100.

As shown in FIG. 11(*b*), when the facial expression recognition application is executed on the display 131, the processor 120 may determine the EMG signal for recognizing the user's facial expression as the biological signal to be input based on the context (recognition of the facial expression) of the electronic device 100. However, when it is necessary to sense a movement of the user's eyes during recognition of the facial expression, the EOG signal may be additionally input using some electrodes around the eye among the electrodes for sensing the EMG signal.

Specifically, even though the electronic device 100 does not include a common electrode, when it is necessary to sense the movement of the user's eyes, the processor 120 may additionally receive the EOG signal by passing a signal input from any one of the electrodes for sensing the EMG signal through a filter corresponding to the EOG signal (a filter for passing only the EOG signal and filtering out the remaining signals).

Here, when it is necessary to sense the movement of the user's eyes includes when it is necessary to accurately sense a movement of muscles around the user's eyes. For example, when the user winks (an operation for closing one eye), a wink motion may not be accurately recognized using the EMG signal only. Therefore, in this case, by receiving the EOG signal additionally, the accuracy of recognition of the facial expression may be further increased. Further, when the user blinks two eyes, whether a corresponding blinking motion is unconscious blinking or conscious blinking may be more accurately recognized by using the additionally recognized EOG signal.

To this end, the processor 120 may separately store a signal (row data) sensed through the electrode for sensing the EMG signal, pass the row data through the filter corresponding to the EOG signal, and additionally receive the EOG signal.

Meanwhile, FIG. 11(*a*) illustrates the embodiment in which the EMG signal is sensed using the reference electrode 34 (an example of sensing a biological signal by unipolar), but the EMG signal may be sensed by using a potential difference of a close electrode pair (an example of sensing a biological signal by bipolar) without the reference electrode 34. More specifically, in order to sense a movement of the user's mouth (a movement of the user's mouth such as '⊥', '⊢', etc. upon pronunciation) using a specific muscle of the user, a method of sensing a biological signal by bipolar may be used other than a method of sensing the biological signal by unipolar.

Figure 12:
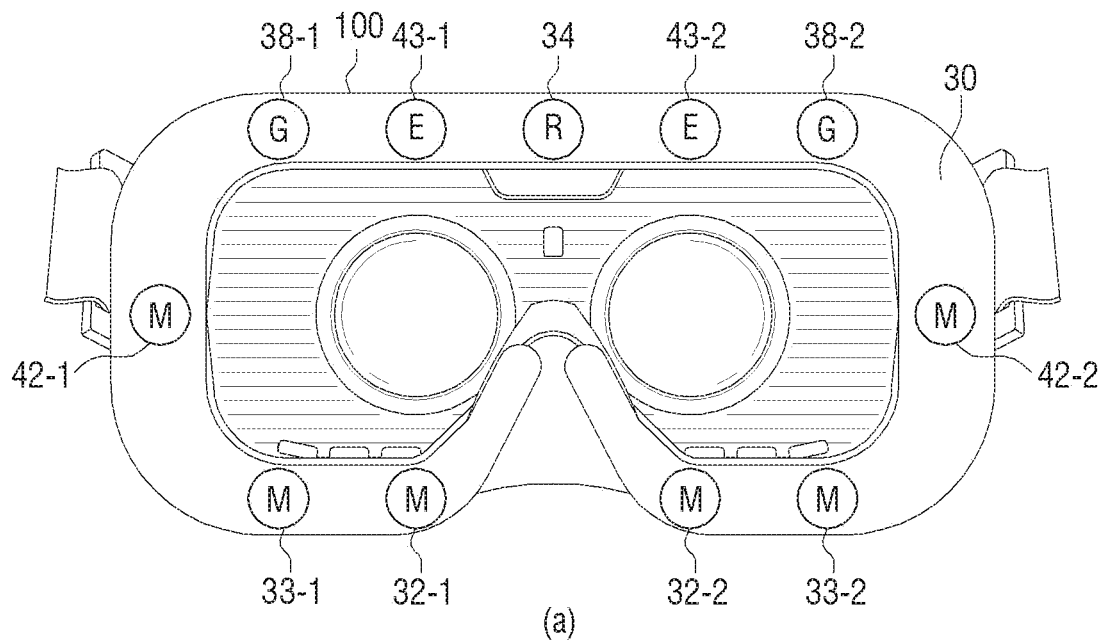
Figure 12:
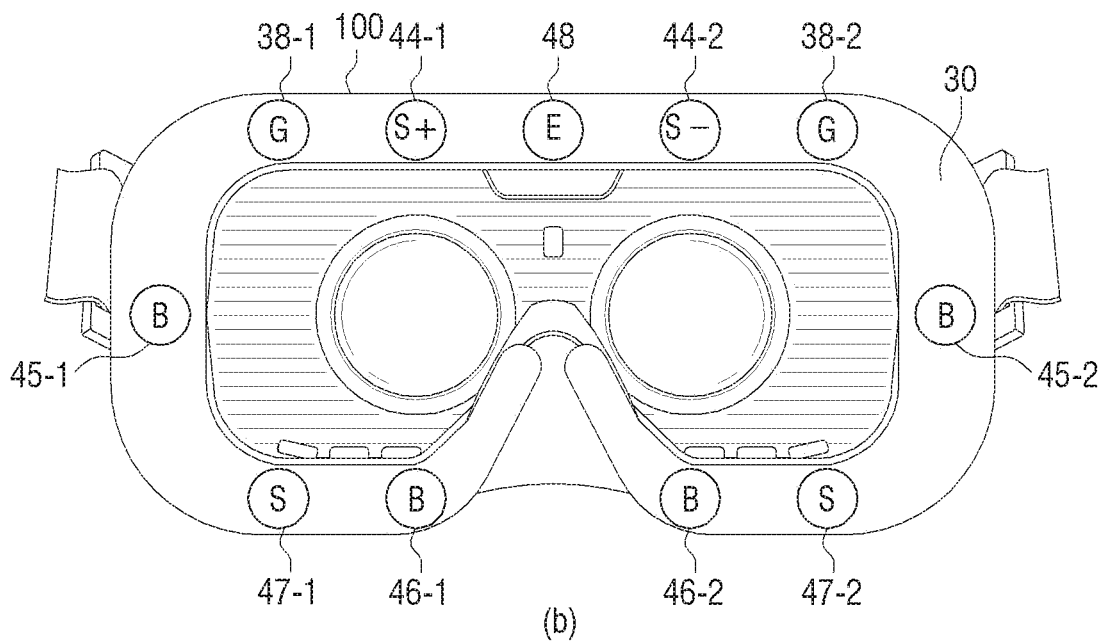

Meanwhile, according to the embodiment shown in FIG. 12(*a*), the electrodes 32-1, 32-2, 33-1, 33-2, 42-1 and 42-2 for sensing the EMG signal, the electrodes 43-1 and 43-2 for sensing an EEG signal, the reference electrode 34 and the ground electrodes 38-1 and 38-2 may be provided on the pad 30 that is in contact with the face of the electronic device 100.

The left electrode 43-1 for sensing the EEG signal and the right electrode 43-2 for sensing the EEG signal may sense concentration/emotion signals occurring in a first front point (hereinafter referred to as fp1) of the frontal region and a second front point (hereinafter referred to as fp2) of the frontal region, respectively.

When it is determined that the context of the electronic device 100 is currently a context requiring emotion recognition (for example, a state in which an application capable of performing emotion recognition has been executed), the processor 120 may determine that the EEG signal for recognizing a user's emotion as the biological signal to be input. The processor 120 may activate a channel corresponding to the electrodes 43-1 and 43-2 for sensing the EEG signal and set a state of the activated channel to an appropriate state for receiving the EEG signal.

Also, according to the embodiment shown in FIG. 12(*b*), the electrodes 44-1 and 44-2 for sensing a GSR signal, the electrodes 45-1, 45-2, 46-1, and 46-2 for sensing a BIA signal, the reference electrode 48, and the ground electrodes 38-1 and 38-2 may be provided on the pad 30 which is in contact with the face of the electronic device 100.

Also, when it is determined that the context of the electronic device 100 is currently the context requiring emotion recognition, the processor 120 may determine the GSR signal and the BIA signal for recognizing the user's emotion as the biological signal to be input. The processor 120 may measure a change in hydration degree of the facial skin through the electrodes 44-1 and 44-2 for sensing the GSR signal and measure a bioelectrical resistance of the facial skin through the electrodes 45-1, 45-2, 46-1, and 46-2 for sensing the BIA signal. To this end, the processor 120 may activate channels respectively corresponding to the electrodes 44-1 and 44-2 for sensing the GSR signal and electrodes 45-1, 45-2, 46-1 and 46-2 for sensing the BIA signal and set a state of each of the activated channels to an appropriate state for receiving the GSR signal and the BIA signal.

Also, electrodes 47-1 and 47-2 for generating an electrical muscle stimulation (EMS) signal may be additionally provided on the pad 30 in contact with the face of the electronic device 100 so as to apply electrical stimulation to the facial muscle. When it is determined that the context of the electronic device 100 is a context requiring to move a specific muscle of the face, the processor 120 may move the specific muscle of the face through the electrodes 47-1 and 47-2 for generating the EMS signal, thereby actively operating the electrodes.

Figure 13:
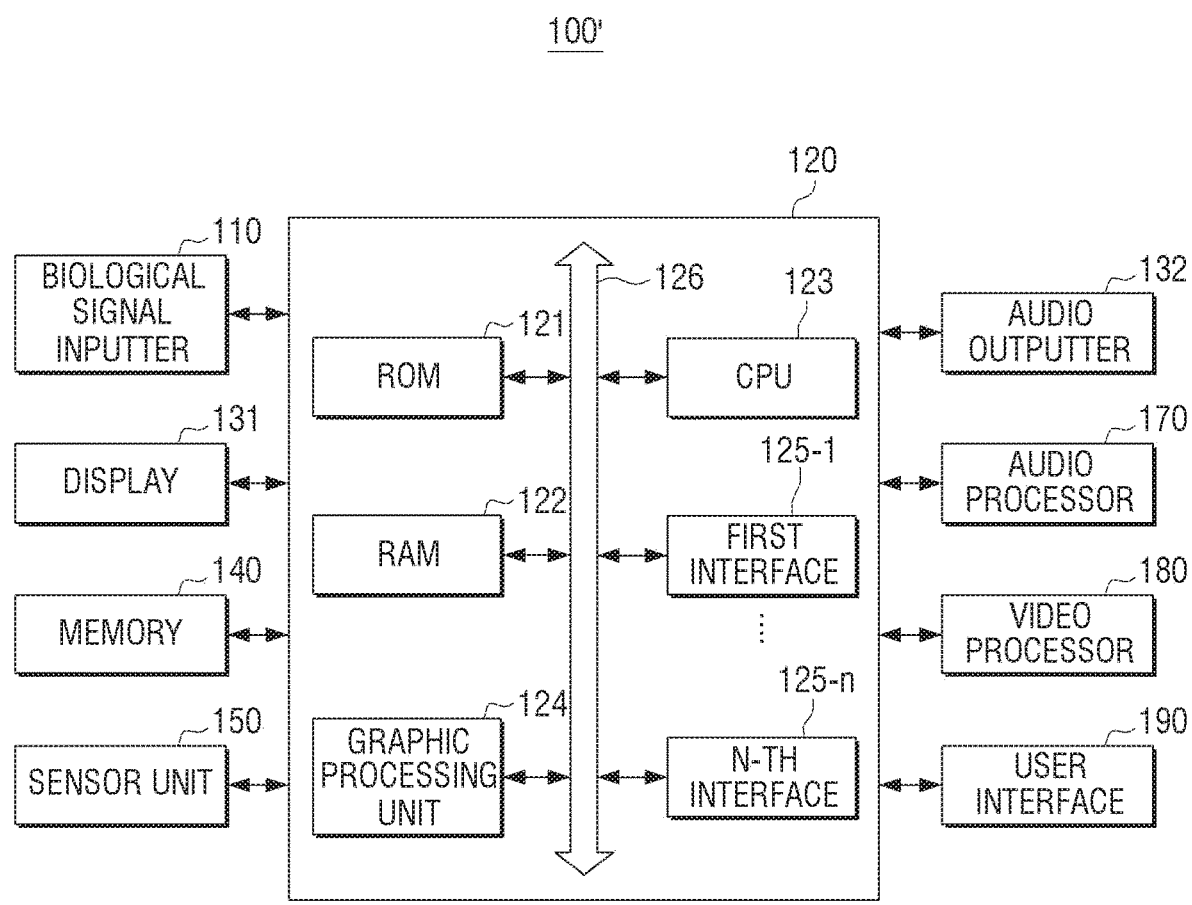
FIG. 13 is a block diagram showing a detailed configuration of an electronic device according to another embodiment of the disclosure.

FIG. 13 is a block diagram showing a detailed configuration of an electronic device according to another embodiment of the disclosure.

As shown in FIG. 13, the electronic device 100' according to another embodiment of the disclosure includes the biological signal inputter 110, the processor 120, the outputter 130, the memory 140, the sensor unit 150, a communicator 160, an audio processor 170, a video processor 180, and a user interface 190. Hereinafter, a redundant description with the description in FIG. 2(*a*) will be omitted.

The processor 120 includes a ROM 121, a RAM 122, a CPU 123, a graphic processing unit 124, and a first interface 125-1 to an n-th interface 125-*n*. The ROM 121, the RAM 122, the CPU 123, the graphic processing unit 124, and the first interface 125-1 to the n-th interface 125-*n* may be connected to each other via a bus 126.

The CPU 123 accesses the storage 140 and performs booting using the O/S stored in the storage 140. The CPU 123 then may perform various operations using various programs, contents, and data stored in the storage 140.

The ROM 121 stores a command set for booting the system and the like. When a turn-on command is input and power is supplied, the CPU 123 copies the O/S stored in the storage 140 to the RAM 122 according to an instruction stored in the ROM 121, executes the O/S, and boots the system. When booting is completed, the CPU 123 copies various application programs stored in the storage 140 to the RAM 122, executes the application programs copied to the RAM 122, and performs various operations.

The graphic processing unit 124 generates a screen including various objects such as an icon, an image, and a text using an operator (not shown) and a renderer (not shown). The operator computes an attribute value such as a coordinate value, a shape, a size, a color, etc. to be displayed by each object according to a layout of a screen. The renderer generates screens of various layouts including the objects based on the attribute values computed by the operator.

The first interface 125-1 to the n-th interface 125-n are connected to the above-described various components. One of the interfaces may be a network interface connected to an external device over a network.

Meanwhile, the operation of the processor 120 described above may be performed by executing the program stored in the storage 140.

The display 131 is a configuration to provide a screen including various contents reproducible in the electronic device 100'. Here, the contents may include contents in various formats such as text, image, moving image, GUI (Graphic User Interface) and the like. In particular, the contents may be implemented as VR contents for providing a 3D image.

The audio outputter 132 is a configuration to output audio processed through the audio processor 170.

The memory 140 may store an O/S software module for driving the electronic device 100' and various data such as various multimedia contents.

Specifically, the memory 140 may store a base module for processing a signal transmitted from each hardware included in the electronic device 100', a storage module for managing a database (DB) or a registry, a graphic processing module for generating a layout screen, a security module, etc.

The sensor unit 150 is a configuration to sense various operations performed in the electronic device 100'. A specific configuration of the sensor unit 150 has been described with reference to FIG. 2(b), and thus a description thereof is omitted below.

The communicator 160 is a configuration to perform communication with an external device according to various types of communication methods and may be implemented separately from the biological signal inputter 110. The communicator 160 may include a Wi-Fi chip, a Bluetooth chip, a wireless communication chip, and the like, and may perform communication with other electronic devices including a server.

The audio processor 170 is a configuration to perform processing on audio data, and the processed audio data is output through the audio outputter 132.

The video processor 180 is a configuration to perform various image processing such as decoding, scaling, noise filtering, frame rate conversion, resolution conversion, and the like on the contents.

The user interface 190 is a configuration to sense a user interaction for controlling the overall operation of the electronic device 100'. The user interface 190 may include a microphone (not shown), a camera (not shown), and the like. The microphone is a configuration for receiving a speech uttered from a user of the electronic device 100' or sound around the electronic device 100'. The user interface 190 may perform an operation of speech recognition, sound recognition or recording operations through the microphone.

Figure 14:
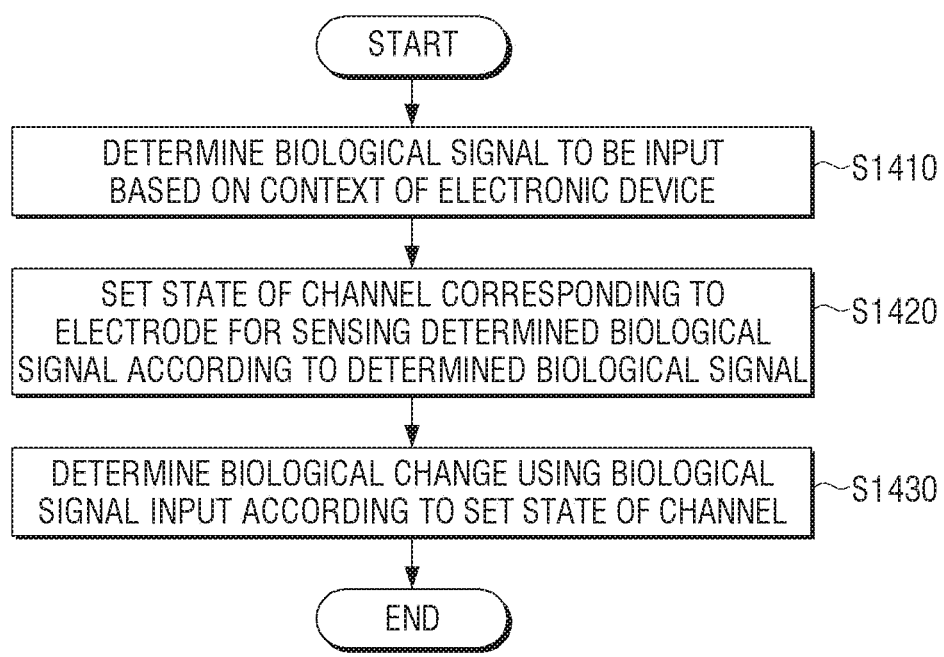
FIG. 14 is a flowchart for explaining a control method of an electronic device according to an embodiment of the disclosure.

FIG. 14 is a flowchart for explaining a control method of an electronic device according to an embodiment of the disclosure.

First, a biological signal to be input is determined based on a context of the electronic device (S1410).

Thereafter, a state of a channel corresponding to an electrode for sensing the determined biological signal is set according to the determined biological signal (S1420). At this time, the channel corresponding to the electrode for sensing the determined biological signal may be activated, and a channel other than the channel corresponding to the electrode for sensing the determined biological signal may be deactivated.

On the other hand, the electrode may include a common electrode used for sensing any one of a plurality of biological signals determined based on the context of the electronic device. For example, the common electrode may be an electrode used for sensing any one biological signal of a safety signal and an EMG signal in a lower side of the user's eyes. In this case, in step S1420, a channel corresponding to the common electrode may be selected as a channel to receive the determined biological signal, and a state of the channel corresponding to the common electrode may be set based on characteristics of the determined biological signal.

In step S1420, based on the characteristics of the determined biological signal, at least one of a sampling rate of the channel corresponding to the electrode for sensing the determined biological signal, an ADC resolution, and a cut-off frequency may be set.

Also, the control method of the electronic device may measure the quality of the biological signal that is first sensed through the electrode, and determine a channel to which the biological signal is input based on the measured quality of the biological signal.

Then, a biological change is determined using the biological signal input according to the set state of the channel (S1430). At this time, the biological change may be determined through a channel corresponding to at least one electrode corresponding to a specific body part according to the context of the electronic device.

Also, the control method of the electronic device may output a result according to the determined biological change. At this time, a screen of a display included in the electronic device may be controlled according to the determined biological change.

According to various embodiments of the disclosure as described above, a biological signal which is required to be sensed may be received according to the context of the electronic device, using only a channel of the corresponding electrode, and a state of the channel may be set in accordance with a characteristic of the biological signal which is required to be sensed, and thus only a desired biological signal may be filtered, thereby reducing an amount of consumption and power consumption for sensing the desired biological signal.

Also, because various biological signals may be sensed according to the context of the electronic device by using the common electrode, the number of necessary electrodes may be reduced, and thus manufacturing cost may be reduced.

The control method according to the above-described various embodiments may be implemented as a program and stored in various recording media. That is, a computer program that may be processed by various processors and may execute the various control methods described above may be stored and used in the recording medium.

For example, a non-transitory computer readable medium storing a program for performing steps of determining a biological signal to be input based on a context of the electronic device, setting a state of a channel corresponding to an electrode for sensing the determined biological signal according to the determined biological signal, and determining a biological change using the biological signal input according to the set state of the channel may be provided.

The non-transitory computer readable medium is not a medium that stores data for a short period of time, such as a register, cache, memory, etc., but is a medium that semi-permanently stores data and is readable by a device. Specifically, the various applications or programs described above may be stored in the non-transitory computer readable medium such as CD, DVD, hard disk, Blu-ray disk, USB, memory card, ROM, etc.

Although the embodiments of the disclosure have been illustrated and described, the disclosure is not limited to the abovementioned specific embodiments, but may be variously modified by those skilled in the art to which the disclosure pertains without departing from the spirit and scope of the disclosure as claimed in the claims. Also, such modifications should also be understood to fall within the scope of the disclosure.

The invention claimed is:

1. An electronic device comprising:
   a biological signal inputter comprising a plurality of electrodes; and
   a processor configured to:
   determine a first biological signal among a plurality of biological signals based on a context of the electronic device,
   based on the first biological signal being determined, identify a channel corresponding to a first electrode as a channel to receive the first biological signal, and activate the channel corresponding to the first electrode for receiving the first biological signal from among the plurality of electrodes,
   based on the first biological signal being determined, deactivate a channel corresponding to a second electrode for receiving a second biological signal of a type different than the first biological signal from among the plurality of electrodes, and
   determine a biological change using the biological signal received through the activated channel,
   wherein the first electrode is used to sense an electrooculogram (EOG) signal, and the second electrode is used to sense an electromyogram (EMG) signal.

2. The electronic device as claimed in claim 1, wherein the processor is further configured to determine the biological change through a channel corresponding to at least one electrode corresponding to a specific body part according to the context of the electronic device.

3. The electronic device as claimed in claim 1,
   wherein the processor is further configured to:
   when the first biological signal is determined, select a channel corresponding to the first electrode as a channel to receive the biological signal, and based on a characteristic of the first biological signal, set a state of the channel corresponding to the first electrode, and
   when the second biological signal is determined, select a channel corresponding to the second electrode as the channel to receive the biological signal and based on a characteristic of the second biological signal, set a state of the channel corresponding to the second electrode.

4. The electronic device as claimed in claim 3,
   wherein the first electrode is used to sense the electrooculogram (EOG) signal at a left side, a right side and an upper side of user's eyes, and
   wherein the second electrode is used to sense the electromyogram (EMG) signal at a lower side of the user's eyes.

5. The electronic device as claimed in claim 1,
   wherein the plurality of electrodes comprise a common electrode used for receiving any one of a plurality of biological signals determined based on the context of the electronic device, and
   wherein the processor is further configured to select a channel corresponding to the common electrode as a channel to receive the first biological signal, and set a state of the channel corresponding to the common electrode based on a characteristic of the first biological signal.

6. The electronic device as claimed in claim 5, wherein the common electrode is used for receiving any one biological signal of the electrooculogram (EOG) signal and the electromyogram (EMG) signal at a lower side of user's eyes.

7. The electronic device as claimed in claim 1, wherein the biological signal comprises at least one of the electromyogram (EMG) signal, the electrooculogram (EOG) signal, an electroencephalogram (EEG) signal, an electrocardiogram (ECG) signal, a Galvanic skin response (GSR) signal, and a bioelectric impedance analysis (BIA) signal.

8. The electronic device as claimed in claim 1, wherein the processor is further configured to set at least one of a sampling rate, an analog-digital converter (ADC) resolution, and a cutoff frequency of the channel corresponding to the first electrode for receiving the first biological signal based on a characteristic of the first biological signal.

9. The electronic device as claimed in claim 1, further comprising:
   an outputter,
   wherein the processor is further configured to control the outputter to output a result according to the determined biological change.

10. The electronic device as claimed in claim 9,
    wherein the outputter comprises a display, and
    wherein the processor is further configured to control a screen of the display according to the determined biological change.

11. The electronic device as claimed in claim 10,
    wherein the context of the electronic device comprises a display state of the display, and
    wherein the processor is further configured to, when the screen of the display is a screen for requesting user authentication using a mouth shape at a time of an utterance:
    determine an EMG signal around a user's mouth as the biological signal to be input, and
    determine the biological change through the channel corresponding to the electrode for receiving the EMG signal.

12. A control method of an electronic device, the control method comprising:
    determining a first biological signal among a plurality of biological signals to be input based on a context of the electronic device;
    based on the first biological signal being determined, identifying a channel corresponding to a first electrode as a channel to receive the first biological signal, ad activating the channel corresponding to the first electrode for receiving the first biological signal from among the plurality of electrodes;
    based on the first biological signal being determined, deactivating a channel corresponding to second electrode for receiving a second biological signal of a type different than the first biological signal from among the plurality of electrodes; and
    determining a biological change using the biological signal received through the activated channel,
    wherein the first electrode is used to sense an electrooculogram (EOG) signal, and the second electrode is used to sense an electromyogram (EMG) signal.

13. The control method as claimed in claim 12, wherein the activating comprises:

when the first biological signal is determined, selecting a channel corresponding to the first electrode as a channel to receive the biological signal, and based on a characteristic of the first biological signal, setting a state of the channel corresponding to the first electrode, and when the second biological signal is determined, selecting a channel corresponding to the second electrode as the channel to receive the biological signal, and based on a characteristic of the second biological signal, setting a state of the channel corresponding to the second electrode.

14. The control method as claimed in claim 12, further comprising:

measuring a signal quality of the first biological signal; and outputting a warning associated with the signal quality.

15. The control method as claimed in claim 12, wherein the biological signal is a signal generated by a human body and is bioelectrical signal which is generated by electrochemical actions of excitable cells which are components of nerve, muscle, and glandular tissues.

\* \* \* \* \*